(12) United States Patent
Pevarello et al.

(10) Patent No.: US 6,784,198 B1
(45) Date of Patent: Aug. 31, 2004

(54) ARYLMETHYL-CARBONYLAMINO-THIAZOLE DERIVATIVES AND THEIR USE AS ANTITUMOR AGENTS

(75) Inventors: Paolo Pevarello, Pavia (IT); Raffaella Amici, Lodi (IT); Manuela Villa, Como (IT); Barbara Salom, Milan (IT); Anna Vulpetti, Milan (IT); Mario Varasi, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 10/048,474

(22) PCT Filed: Aug. 11, 2000

(86) PCT No.: PCT/IB00/01423

§ 371 (c)(1),
(2), (4) Date: Jul. 18, 2002

(87) PCT Pub. No.: WO01/14353

PCT Pub. Date: Mar. 1, 2001

Related U.S. Application Data

(63) Continuation-in-part of application No. 09/372,832, filed on Aug. 12, 1999, now Pat. No. 6,114,365.

(51) Int. Cl.$^7$ .................... A61K 31/425; A61K 31/495; C07D 277/04; C07D 401/00
(52) U.S. Cl. .................. 514/371; 514/252.01; 548/195; 544/238
(58) Field of Search ................................. 514/371, 252, 514/252.01; 548/195; 544/369, 238

(56) References Cited

U.S. PATENT DOCUMENTS 6,114,365 A    9/2000  Pevarello et al.

FOREIGN PATENT DOCUMENTS

| WO | 98 04536 | 5/1998 |
| WO | 99 21845 | 5/1999 |
| WO | 99 24416 | 5/1999 |
| WO | 00 26202 | 5/2000 |

*Primary Examiner*—Deborah C. Lambkin
(74) *Attorney, Agent, or Firm*—Scully, Scott, Murphy & Presser

(57) ABSTRACT

2-amino-1,3-thiazole derivatives represented by formula (I) or (II): where R, $R_1$, $R_2$ and $R_3$ are defined herein, or pharmaceutically acceptable salts thereof are useful as, for example, the treatment of cancer, cell proliferative disorders, Alzheimer's disease, viral infections, auto-immune diseases or neurodegenerative diseases.

17 Claims, No Drawings

ARYLMETHYL-CARBONYLAMINO-THIAZOLE DERIVATIVES AND THEIR USE AS ANTITUMOR AGENTS

This application is a 371 of PCT/IB00/01423 filed Aug. 11, 2000 and is a continuation-in-part of Ser. No. 09/372,832 filed Aug. 12, 1999, now U.S. Pat. No. 6,114,365.

BACKGROUND OF THE INVENTION

1. Field of the Invention

The present invention relates to arylmethyl-carbonylaminothiazole derivatives and, more specifically relates to 2-(arylmethyl-carbonylamino)-1,3-thiazole derivatives, to a process for their preparation, to pharmaceutical compositions containing them, and to their use as therapeutic agents, particularly in the treatment of cancer and cell proliferative disorders.

2. Background of the Invention

Several cytotoxic drugs such as, e.g. fluorouracil (5-FU), doxorubicin and camptothecins, cause damage DNA or affect cellular metabolic pathways and thus cause, in many cases, an indirect block of the cell cycle. Therefore, by producing an irreversible damage to both normal and tumor cells, these agents result in a significant toxicity and side-effects.

In this respect, compounds capable of being highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the cyclin-dependent kinases (cdk).

In their turn, the cdks themselves are regulated at many levels such as, for instance, binding to cyclins.

The coordinated activation and inactivation of different cyclin/cdk complexes is necessary for normal progression through the cell cycle. Both the critical G1-S and G2-M transitions are controlled by the activation of different cyclin/cdk activities. In G1, both cyclin D/cdk4 and cyclin E/cdk2 are thought to mediate the onset of S-phase. Progression through S-phase requires the activity of cyclin A/cdk2 whereas the activation of cyclin A/cdc2 (cdk1) and cyclin B/cdc2 are required for the onset of metaphases. For a general reference to cyclins and cyclin-dependent kinases see, for example, Kevin R. Webster et al. in Exp. Opin. Invest. Drugs, 1998, Vol. 7(6), 865–887.

Checkpoint controls are defective in tumor cells due, in part, to disregulation of cdk activity. For example, altered expression of cyclin E and cdk's has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

SUMMARY OF THE INVENTION

It is an object of the invention to provide compounds which are useful in treating cell proliferative disorders associated with an altered cell dependent kinase activity. It is another object to provide compounds which have cdk/cyclin kinase inhibitory activity.

It is another object of the invention to provide compounds which are useful in therapy as antitumor agents but lack, in terms of both toxicity and side effects, the drawbacks associated with currently available antitumor drugs discussed above.

The present inventors have now discovered that 2-amino-1,3-thiazole derivatives are endowed with cdk/cyclin kinase inhibitory activity and are thus useful in therapy as antitumor agents and lack, in terms of both toxicity and side effects, the aforementioned drawbacks associated with currently available antitumor drugs.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Due to the key role of cdks in the regulation of cellular proliferation, the 2-amino-1,3-thiazole derivatives are also useful in the treatment of a variety of cell proliferative disorders such as, for instance, benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (J. Biochem., 17, 741–749, 1995).

The compounds of this invention, as modulators of apoptosis, could be useful in the treatment of cancer, viral infections, prevention of AIDS development in HIV-infected individuals, autoimmune diseases and neurodegenerative disorder.

The compounds of this invention may also be useful in inhibiting tumor angiogenesis and metastasis.

The compounds of this invention may also act as inhibitors of other protein kinases, e.g. protein kinase C, her2, raf1, MEKI, MAP kinase, EGF receptor, PDGF receptor, IGF receptor, P13 kinase, weel kinase, Src, Abl and thus be effective in the treatment of diseases associated with other protein kinases.

Accordingly, the present invention provides a method for the treatment of cell proliferative disorders associated with an altered cell dependent kinase activity, by administering to a mammal in need thereof an effective amount of a 2-amino-1,3-thiazole represented by formula (I) or (II):

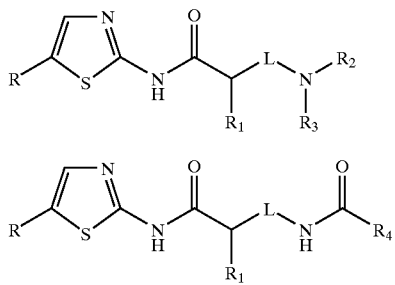

where
L is a phenyl group or a 5 or 6 membered aromatic heterocycle with one or more heteroatoms selected from the group consisting of nitrogen, oxygen and sulfur;

R is (i) a halogen atom, a nitro group, or it is selected from the group consisting of pyrrolidino, morpholino, piperazino, N-alkyl piperazino, N-aryl-piperazino, N-arylalkyl-piperazino, piperidino and azabicyclo [3.2.2]nonane; or (ii) an amino group optionally further substituted with one or more groups, which may be the same or different, selected from the group consisting of alkyl, aryl, arylalkyl, alkylsulphonyl, arylsulphonyl, arylalkylsulphonyl, alkylcarbonyl, arylcarbonyl, and arylalkylcarbonyl, wherein the alkyl moieties therein are optionally further substituted with one or more hydroxy or amino groups; or (iii) a $C_3$–$C_6$ cycloalkyl optionally substituted with a straight or branched $C_1$–$C_6$ alkyl group; or (iv) a straight or branched $C_1$–$C_6$ alkyl group or an arylalkyl group which is optionally substituted with one or more substituents selected from the group consisting of halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl, arylalkylcarbonyl, alkylsulphonyl, arylsulphonyl, arylalkylsulphonyl, aminosulphonyl, alkylaminosulphonyl, dialkylaminosulphonyl, alkylcarbonylamino, arylalkylcarbonylamino, arylaminosulphonyl, arylalkylaminosulphonyl, arylcarbonylamino, alkylsulphonylamino, arylsulphonylamino, arylalkylsulphonylamino, alkoxycarbonyl, aryloxycarbonyl, aminocarbonyl, alkylaminocarbonyl, arylaminocarbonyl, dialkylaminocarbonyl, arylalkylaminocarbonyl, pyrrolidino, morpholino, piperazino, N-alkylpiperazino, N-aryl-piperazino, N-arylalkyl-piperazino, piperidino, and azabicyclo[3.2.2]nonane; or (v) an aryl group which is optionally substituted with one or more substituents selected from the group consisting of halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl, arylalkylcarbonyl, alkylsulphonyl, arylsulphonyl, arylalkylsulphonyl, aminosulphonyl, alkylaminosulphonyl, dialkylaminosulphonyl, alkylcarbonylamino, arylalkylcarbonylamino, arylaminosulphonyl, arylalkylaminosulphonyl, arylcarbonylamino, alkylsulphonylamino, arylsulphonylamino, arylalkylsulphonylamino, alkoxycarbonyl, aryloxycarbonyl, aminocarbonyl, alkylaminocarbonyl, arylaminocarbonyl, dialkylaminocarbonyl, arylalkylaminocarbonyl, pyrrolidino, morpholino, piperazino, N-alkylpiperazino, N-aryl-piperazino, N-arylalkyl-piperazino, piperidino, and azabicyclo[3.2.2]nonane;

$R_1$ is a hydrogen atom or a straight or branched $C_1$–$C_4$ alkyl group optionally substituted with one or more hydroxy, alkoxy, amino, alkylamino, or dialkylamino groups;

$R_2$ and $R_3$, which may be the same or different, are a hydrogen atom, a cycloalkyl group, a straight or branched $C_1$–$C_6$ alkyl group or an aryl group, which are each optionally substituted as described above for R; or $R_2$ and $R_3$, together with the nitrogen atom to which they are bonded, form a 4-morpholinyl, 1-piperazinyl, N-alkyl-piperazinyl, N-aryl-piperazinyl, N-arylalkyl-piperazinyl, piperidinyl, pyrrolidinyl, 2-oxo-1-pyrrolidinyl, imidazolyl or 3-azabicyclo[3.2.2]nonyl ring;

$R_4$ is carboxy, a perfluorinated alkyl group, a $C_2$–$C_4$ alkynyl group, 2-oxo-pyrrolidinyl, piperidinyl or a straight or branched $C_1$–$C_6$ alkyl group or an aryl group, which is optionally substituted as described above for R;

or a pharmaceutically acceptable salt thereof.

In a preferred embodiment of the invention, the cell proliferative disorder is selected from the group consisting of cancer, Alzheimer's disease, viral infections, autoimmune diseases or neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis, and post-surgical stenosis and restenosis.

In addition, the inventive method may provide for tumor angiogenesis and metastasis inhibition. The inventive method may also provide for cell cycle inhibition or cdk/cyclin dependent inhibition.

The present invention also provides a 2-amino-1,3-thiazole represented by formula (I) or (II):

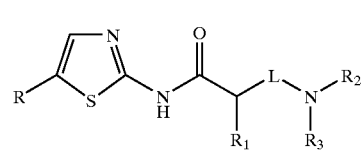

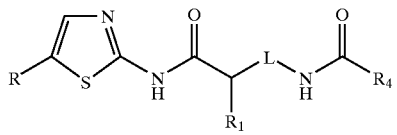

(II)

where
L is a phenyl group or a 5 or 6 membered aromatic heterocycle with one or more heteroatoms selected from the group consisting of nitrogen, oxygen and sulfur;

R is (i) a halogen atom, a nitro group, or it is selected from the group consisting of pyrrolidino, morpholino, piperazino, N-alkyl, piperazino, N-aryl-piperazino, N-arylalkyl-piperazino, piperidino. and azabicyclo [3.2.2]nonane, or (ii) an amino group optionally further substituted with one or more groups, which are the same or different, selected from the group consisting of alkyl, aryl, arylalkyl, alkylsulphonyl, arylsulphonyl, arylalkylsulphonyl, alkylcarbonyl, arylcarbonyl, and arylalkylcarbonyl, wherein the alkyl moiety therein is optionally further substituted with one or more hydroxy or amino groups; or (iii) a C3–C6 cycloalkyl optionally substituted with a straight or branched $C_1$–$C_6$ alkyl group; or (iv) a straight or branched $C_1$–$C_6$ alkyl group or an arylalkyl group, which is optionally substituted with one or more halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl, arylalkylcarbonyl, alkylsulphonyl, arylsulphonyl, arylalkylsulphonyl, aminosulphonyl, alkylaminosulphonyl, arylaminosulphonyl, dialkylaminosulphonyl, alkyl carbonylamino, arylalkylaminosulphonyl, arylcarbonylamino, arylalkylcarbonylamino, alkylsulphonylamino, arylsulphonylamino, arylalkylsulphonylamino, alkoxycarbonyl, aryloxycarbonyl, aminocarbonyl, alkylaminocarbonyl, dialkylaminocarbonyl, arylaminocarbonyl, arylalkylaminocarbonyl, pyrrolidino, morpholino, piperazino, N-alkylpiperazino, N-aryl-piperazino, N-arylalkyl-piperazino, piperidino or azabicyclo[3.2.2]nonane substituents; or (v) an aryl group optionally substituted with one or more substituents selected from the group consisting of halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl, arylalkylcarbonyl, alkylsulphonyl, arylsulphonyl, arylalkylsulphonyl, aminosulphonyl, alkyl aminosulphonyl, arylaminosulphonyl, dialkylaminosulphonyl, alkylcarbonylamino, arylalkylaminosulphonyl, arylcarbonylamino, arylalkylcarbonylamino, alkylsulphonylamino, arylsulphonylamino, arylalkylsulphonylamino, alkoxycarbonyl, aryloxycarbonyl, aminocarbonyl, alkylaminocarbonyl, dialkylaminocarbonyl, arylaminocarbonyl, arylalkylaminocarbonyl, pyrrolidino, morpholino, piperazino, N-alkylpiperazino, N-aryl-piperazino, N-arylalkyl-piperazino, piperidino and azabicyclo[3.2.2]nonane;

$R_1$ is a hydrogen atom or a straight or branched $C_1$–$C_4$ alkyl group optionally substituted with one or more hydroxy, alkoxy, amino, alkylamino, or dialkylamino group;

$R_2$ and $R_3$, which may be the same or different, are a hydrogen atom, a cycloalkyl group, a straight or branched $C_1$–$C_6$ alkyl group or an aryl group, which are each optionally substituted as described above for R; or $R_2$ and $R_3$, together with the nitrogen atom to which they are bonded, form a 4-morpholinyl, 1-piperazinyl, N-alkyl-piperazinyl, N-aryl-piperazinyl, N-arylalkyl-piperazinyl, piperidinyl, pyrrolidinyl, 2-oxo-1-pyrrolidinyl, imidazolyl or 3-azabicyclo[3.2.2]nonyl ring;

$R_4$ is carboxy, a perfluorinated alkyl group, a $C_2$–$C_4$ alkenyl group, a $C_2$-$C_4$ alkynyl group, 2-oxopyrrolidinyl, piperidinyl or a straight or branched $C_1$–$C_6$ alkyl group or an aryl group, which is optionally substituted as described above for R;

or a pharmaceutically acceptable salt thereof.

The present invention also provides a process for preparing the 2-amino-1,3-thiazole derivative described above, or a pharmaceutically acceptable salt thereof, by:

reacting a compound represented by formula (III):

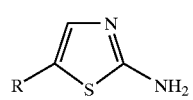

(III)

with a compound represented by formula (IV):

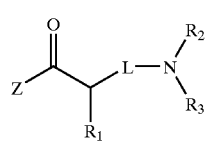

(IV)

where
R, L, $R_1$, $R_2$ and $R_3$ are as defined above, and
Z is hydroxy or a suitable leaving group, to produce a 2-amino-1,3-thiazole derivative represented by formula (1), where R, L, $R_1$, $R_2$ and $R_3$ are as defined above.

The present invention also provides a process for preparing the 2-amino-1,3-thiazole derivative described above, or a pharmaceutically acceptable salt thereof, by:

reacting a compound represented by formula (I):

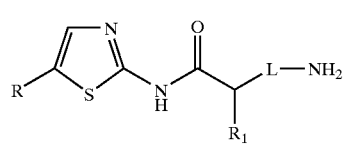

(I)

with a compound represented by formula (V):

$R_4$—COX (V)

where

R, $R_1$, L and $R_4$ are as defined above, and

X is hydroxy or a suitable leaving group, such as chlorine or bromine, to produce a 2-amino-1,3-thiazole derivative represented by formula (II), where R, L, $R_1$ and $R_4$ are as defined above.

The present invention also provides a process for preparing the 2-amino-1,3-thiazole derivative described above, or a pharmaceutically acceptable salt thereof, by:

reacting a 2-amino-1,3-thiazole derivative represented by formula (I), where both or at least one of $R_2$ and $R_3$ is a hydrogen atom, with a compound represented by formula (VI):

$$R'Y \quad (VI)$$

where

R' has the meanings of $R_2$ or $R_3$ but is other than hydrogen, and

Y is a suitable leaving group, to produce a 2-amino-1,3-thiazole derivative of formula (I) where both or at least one of $R_2$ and $R_3$ is other than hydrogen; and, optionally, converting a 2-amino-1,3-thiazole derivative represented by formula (I) or (II) into another 2-amino-1,3-thiazole derivative represented by formula (I) or (II), and/or into a salt thereof.

The present invention also provides a pharmaceutical composition, containing the 2-amino-1,3-thiazole derivative described above and at least one pharmaceutically acceptable carrier and/or diluent.

A more complete appreciation of the invention and many of the attendant advantages thereof will be readily obtained as the same becomes better understood by reference to the following detailed description.

DETAILED DESCRIPTION OF THE INVENTION

Several 2-amino-1,3-thiazoles are known as herbicides, synthetic intermediates or even as therapeutic agents. Among them are, as an example, 2-benzamido-1,3-thiazoles known as antiallergic agents (EP-A-261503, Valeas S. P. A.); 5-alkyl-2-phenylalkylcarbonylamino-1,3-thiazoles known as protein kinase C inhibitors (WO 98/04536, Otsuka Pharmaceutical Co.); 5-arylthio-2-acylamino-1,3-thiazoles known as antitumor agents (EP-A412404, Fujisawa Pharm. Co.); 4-amino-2-carbonylamino-1,3-thiazoles known as cyclin-dependent kinases inhibitors (WO 99/21845, Agouron Pharmaceuticals Inc.).

As used herein, unless otherwise specified, the term halogen atom refers to a fluorine, chlorine, bromine or iodine atom.

As used herein and unless otherwise indicated, the terms alkyl and alkoxy include $C_1$–$C_6$ alkyl and C1–C6 alkoxy groups. The term straight or branched includes a $C_1$–$C_6$ alkyl or $C_1$–$C_6$ alkoxy group selected from methyl, ethyl, n-propyl, isopropyl, n-butyl, isobutyl, sec-butyl, tertbutyl, n-pentyl, n-hexyl, methoxy, ethoxy, n-propoxy, isopropoxy, n-butoxy and the like.

Likewise, the term N-alkyl-piperazinyl, alkylsulphonyl, alkylcarbonyl, alkylthio, dialkylamino, alkoxyamino, arylalkyl, alkylamino, alkyl-cycloalkyl, alkoxycarbonyl, alkoxycarbonylamino and the like, includes the aforementioned groups where the alkyl and alkoxy moieties have, for example, $C_1$–$C_6$ alkyl or alkoxy groups.

Unless otherwise specified, the term cycloalkyl refers to a $C_3$–$C_6$ cycloalkyl group, such as cyclopropyl, cyclobutyl, cyclopentyl and cyclohexyl as well as cycloalkyl and bridged cycloalkyl groups with up to 10 carbon atoms such as, for instance, adamantane group.

The term aryl includes mono-, bi- or poly- carbocyclic or heterocyclic hydrocarbons with from 1 to 4 ring moieties, wherein at least one of the rings is aromatic, either fused or linked to each other by single bonds. Thus, these groups may have from 5 to 20 carbon atoms, preferably from 6 to 20 carbon atoms.

The term heterocycle, hence encompassing heteroaromatic rings, includes a 5 or 6 membered saturated or unsaturated carbocycles wherein one or more carbon atoms are replaced by one or more atoms selected from nitrogen, oxygen and sulphur.

Example of preferred aryl groups are phenyl, 1-naphthyl, 2-naphthyl, indanyl, indenyl, biphenyl, benzocycloalkyl, e.g. bicyclo[4.2.0]octa-1,3,5, -triene, benzoheterocyclyl, e.g. benzodioxolyl, quinoxalyl, indolyl, optionally benzocondensed pyrrolyl, furyl, thienyl, imidazolyl, pyrazolyl, thiazolyl, oxazolyl, isoxazolyl, tetrazolyl, pyridyl, pyrazinyl, pyrimidyl and the like.

The term $C_2$–$C_4$ alkenyl or alkynyl includes a group selected from vinyl, allyl, 1-propenyl, isopropenyl, 1-butanol, 2-butenyl, 3-butenyl, ethynyl, propynyl, butynyl and the like.

The term perfluorinated alkyl and alkoxy group refers to a $C_1$–$C_4$ alkyl or alkoxy group further substituted by more than one fluorine atom such as, for instance, trifluoromethyl, 2,2,2-trifluoroethyl, 1,1,2,2,2-pentafluoroethyl, trifluoromethoxy and the like.

Pharmaceutically acceptable salts of the compounds of formula (I) or (II) include the acid addition salts with inorganic or organic, e.g. nitric, hydrochloric, hydrobromic, sulphuric, perchloric, phosphoric, acetic, trifluoroacetic, propionic, glycolic, lactic, oxalic, malonic, malic, maleic, tartaric, citric, benzioic, cinnamic, mandelic, methanesulphonic, isethionic and salicylic acid, as well as the salts with inorganic or organic bases, e.g. alkali or alkaline-earth metals, especially sodium, potassium, calcium or magnesium hydroxides, carbonates or bicarbonates, acyclic or cyclic amines, preferably methylamine, ethylamine, diethylamine, triethylamine or piperidine.

The compounds of formula (I) or (II) may have asymmetric carbon atoms and may therefore exist either as racemic admixtures or as individual optical isomers.

Accordingly, the use as an antitumor agent of all the possible isomers and their admixtures and of both the metabolites and the pharmaceutically acceptable bioprecursors (otherwise referred to as pro-drugs) of the compounds of formula (I) or (II) are also within the scope of the present invention.

Preferred compounds of the invention of formula (I) or (II) are those in which L is phenyl, thiazole, imidazole, oxazole, pyrazole, isoxazole, thiophene, pyridine or pyrimidine; R is (i) a halogen atom, (ii) a group selected from arylamino, alkylamino or dialkylamino wherein the alkyl moiety can be further substituted with one or more hydroxy or amino groups, (iii) a $C_3$–$C_6$ cycloalkyl group optionally substituted by an alkyl group, (iv) a straight or branched $C_1$–$C_4$ alkyl or arylalkyl group, each optionally substituted as above indicated, (v) an optionally substituted aryl group; $R_1$ is hydrogen or a $C_1$–$C_4$ alkyl group optionally substituted with hydroxy or amino.

Still more preferred compounds, within this class, are the compounds of formula (I) or (II) where L is phenyl or thiazole; R is selected from the group consisting of alkylamino or dialkylamino, wherein the alkyl moiety can be further substituted with one or more hydroxy or amino groups, $C_3$–$C_6$ cycloalkyl, straight or branched $C_1$–$C_4$ alkyl optionally substituted with one or more hydroxy, amino, alkylamino, dialkylamino, pyrrolidino, morpholino, N-alkylpiperazino, azabicyclo[3.2.2]nonane; $R_1$ is hydrogen; $R_2$ and $R_3$ are, the same or different, hydrogen, adamantyl, straight or branched $C_1$–$C_6$ alkyl optionally substituted with one or more hydroxy, alkoxy, amino, alkylamino, dialkylamino, pyrrolidino, morpholino, N-alkyl-piperazino, imidazole, 3-azabicyclo[3.2.2]nonane, aminocarbonyl, dialkylaminocarbonyl; or, taken together with the nitrogen atom to which they are linked, $R_2$ and $R_1$ form a 4-morpholinyl, N-alkyl-piperazinyl, pyrrolidinyl, 2-oxo-1-pyrrolidinyl, imidazolyl or 3-azabicyclo[3.2.2]nonyl ring; and $R_4$ is carboxy, perfluorinated alkyl, $C_2$–$C_4$-alkenyl, $C_2$–$C_4$-alkynyl, 2-oxopyrrolidinyl, piperidinyl, aryl optionally substituted with halogen, dialkylamino, aminosulfonyl, aminocarbonyl, alkoxy, hydroxy, alkylcarbonylamino, amino, pyrrolidino, N-alkyl-piperazino, morpholino; or $R_4$ is a straight or branched $C_1$–$C_6$ alkyl group optionally substituted with halogen, hydroxy, alkoxy, alkylthio, arylthio, $C_3$–$C_6$ cycloalkyl, cyano, carboxy, amino, alkylamino, dialkylamino, pyrrolidino, morpholino, N-alkylpiperazino, azabicyclo[3.2.2]nonane, aminocarbonyl, alkylaminocarbonyl, dialkylaminocarbonyl, aryl optionally substituted with halogen, dialkylamino, aminosulfonyl, aminocarbonyl, alkoxy, hydroxy, alkylcarbonylamino, amino, alkylamino, pyrrolidino, N-alkyl-piperazino or morpholino.

Examples of preferred compounds of formula (I) or (II) of the invention, which may be in the form of pharmaceutically acceptable salts, e.g., hydrobromide or hydrochloride, include the following:

N-(4-{2-[(5-isopropyl-1,3-thiazol-2-yl)amino]-2-oxoethyl}-1,3-thiazol-2-yl)acrylamide;

N-(4-{2-[(5-isopropyl-1,3-thiazol-2-yl)amino]-2-oxoethyl}-1,3-thiazol-2-yl)-2-methylpropanamide;

N-(4-{2-[(5-isopropyl-1,3-thiazol-2-yl)amino]-2-oxoethyl}-1,3-thiazol-2-yl)-2-naphthamide;

N-(4-{2-[(5-isopropyl-1,3-thiazol-2-yl)amino]-2-oxoethyl}-1,3-thiazol-2-yl)-2-benzamide;

N-(4-{2-[(5-isopropyl-1,3-thiazol-2-yl)amino]-2-oxoethyl}-1,3-thiazol-2-yl)-2-phenylacetamide;

N-(4-{2-[(5-isopropyl-1,3-thiazol-2-yl)amino]-2-oxoethyl}-1,3-thiazol-2-yl)-2-(3-pyridinyl)acetamide;

2,2,3,3,3-pentafluoro-N-(4-{2-[(5-isopropyl-1,3-thiazol-2-yl)amino]-2-oxoethyl}-1,3thiazol-2-yl)propanamide, 2-[(4-{2-[(5-isopropyl-1,3-thiazol-2-yl)amino]-2-oxoethyl}-1,3-thiazol-2-yl)amino]-2-oxoacetic acid;

2-fluoro-N-(4-{2-[(5-isopropyl-1,3-thiazol-2-yl)amino]-2-oxoethyl}-1,3-thiazol-2-yl)acetamide;

2-chloro-N-(4-{2-[(5-isopropyl-1,3-thiazol-2-yl)amino]-2-oxoethyl}-1,3-thiazol-2-yl)acetamide;

2-cyano-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-3-oxo-beta-alanine;

N'1'-(4-{2-[(5-isopropyl-1,3-thiazol-2-yl)amino]-2-oxoethyl}-1,3-thiazol-2-yl)malonamide;

4-[(4-{2-[(5-isopropyl-1,3-thiazol-2-yl)amino]-2-oxoethyl}-1,3-thiazol-2-yl)-4-oxo-outanoic acid;

2-[2-(glycoloylamino)-1,3-thiazol-4-yl]-N-(5-isopropyl-1,3-thiazol-2-yl)acetamide;

3-hydroxy-N-(4-{2-[(5-isopropyl-1,3-thiazol-2-yl)amino]-2-oxoethyl}-1,3-thiazol-2-yl)propanamide;

3-amino-N-(4-{2-[(5-isopropyl-1,3-thiazol-2-yl)amino]-2-oxoethyl}-1,3-thiazol-2-yl)propanamide;

2-amino-N-(4-{2-[(5-isopropyl-1,3-thiazol-2-yl)amino]-2-oxoethyl}-1,3-thiazol-2-yl)acetamide;

4-hydroxy-N-(4-{2-[(5-isopropyl-1,3-thiazol-2-yl)amino]-2-oxoethyl}-1,3-thiazol-2-yl)butanamide;

4-amino-N-(4-{2-[(5-isopropyl-1,3-thiazol-2-yl)amino]-2-oxoethyl}-1,3-thiazol-2-yl)butanamide;

N-(4-{2-[(5-isopropyl-1,3-thiazol-2-yl)amino]-2-oxoethyl}-1,3-thiazol-2-yl)-2-(4-methyl-1-piperazinyl)acetamide;

2-(4-benzyl-1-piperazinyl)-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-2-(1-piperidinyl)acetamide;

N-(5-isopropyl-1,3-thiazol-2-yl)-2-[2-(2-oxo-1-pyrrolidinyl)-1,3-thiazol-4-yl]acetamide;

2-[4-(dimethylamino)phenyl]-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-2-(1H-1,2,3,4-tetraazol-1-yl)acetamide;

N-(4-{2-[(5-isopropyl-1,3-thiazol-2-yl)amino]-2-oxoethyl}-1,3-thiazol-2-yl)-5-oxo-2-pyrrolidinecarboxamide;

N'1'-(4-{2-[(5-isopropyl-1,3-thiazol-2-yl)amino]-2-oxoethyl}-1,3-thiazol-2-yl)succinamide;

3-(1H-benzimidazol-2-yl)-N-(4-{2-[(5-isopropyl-1,3-thiazol-2-yl)amino]-2-oxoethyl}-1,3-thiazol-2-yl)propanamide;

1-acetyl-N-(4-{2-[(5-isopropyl-1,3-thiazol-2-yl)amino]-2-oxoethyl}-1,3-thiazol-2-yl)-4-piperidinecarboxamide;

2-[2-(acetylamino)-1,3-thiazol-4-yl]-N-(5-isopropyl-1,3-thiazol-2-yl)acetamide;

4-chloro-N-(4-{2-[(5-isopropyl-1,3-thiazol-2-yl)amino]-2-oxoethyl}-1,3-thiazol-2-yl)butanamide;

N-(4-{2-[(5-isopropyl-1,3-thiazol-2-yl)amino]-2-oxoethyl}-1,3-thiazol-2-yl)-2-methoxyacetamide;

3,3,3-trifluoro-N-(4-{2-[(5-isopropyl-1,3-thiazol-2-yl)amino]-2-oxoethyl}-1,3-thiazol-2-yl)propanamide 2-(dimethylamino)-N-(4-{2-[(5-isopropyl-1,3-thiazol-2-yl)amino]-2-oxoethyl}-1,3-thiazol-2-yl)acetamide N-(5-isopropyl-1,3-thiazol-2-yl)-2-(2-{[2-(4-methyl-1-piperazinyl)ethyl]amino}-1,3-thiazol-4-yl)acetamide N-(5-isopropyl-1,3-thiazol-2-yl)-2-(2-{methyl[2-(4-methyl-1-piperazinyl)ethyl]amino}-1,3-thiazol-4-yl)acetamide;

N-(5-isopropyl-1,3-thiazol-2-yl)-2-(2-{[2-(4-morpholinyl)ethyl]amino}-1,3-thiazol-4-yl)acetamide;

N-(5-isopropyl-1,3-thiazol-2-yl)-2-(2-{methyl[2-(4-morpholinyl)ethyl]amino}-1,3-thiazol-4-yl)acetamide;

2-{2-[(2,3-dihydroxypropyl)amino]-1,3-thiazol-4-yl}-N-(5-isopropyl-1,3-thiazol-2-yl)acetamide;

2-{2-[(2,3-dihydroxypropyl)(methyl)amino]-1,3-thiazol-4-yl}-N-(5-isopropyl-1,3-thiazol-2-yl)acetamide;

2-(2-{[3-(dimethylamino)-2-hydroxypropyl]amino}-1,3-thiazol-4-yl)-N-(5-isopropyl-1,3-thiazol-2-yl)acetamide;

2-{2-[(2-amino-2-oxoethyl)amino]-1,3-thiazol-4-yl}-N-(5-isopropyl-1,3-thiazol-2-yl)acetamide;

2-(2-{[2-(dimethylamino)-2-oxoethyl]amino}-1,3-thiazol-4-yl)-N-(5-isopropyl-1,3-thiazol-2-yl)acetamide;

2-[2-(adamantylamino)-1,3-thiazol-4-yl]-N-(5-isopropyl-1,3-thiazol-2-yl)acetamide;

2-[4-(dimethylamino)phenyl]-N-(5-isopropyl-1,3-thiazol-2-yl)acetamide;

N-(5-isopropyl-1,3-thiazol-2-yl)-2-[4-(4-methyl-1-piperazinyl)phenyl]acetamide;

N-(5-isopropyl-1,3-thiazol-2-yl)-2-[4-(4-morpholinyl)phenyl]acetamide;

N-(5-isopropyl-1,3-thiazol-2-yl)-2-[4-(1-pyrrolidinyl)phenyl]acetamide;

N-(5-isopropyl-1,3-thiazol-2-yl)-2-(4-{[2-(4-methyl-1-piperazinyl)ethyl]amino}phenyl)acetamide;

N-(5-isopropyl-1,3-thiazol-2-yl)-2-(4-{methyl[2-(4-methyl-1-piperazinyl)ethyl]amino}phenyl)acetamide;

N-(5-isopropyl-1,3-thiazol-2-yl)-2-(4-{[2-(4-morpholinyl)ethyl]amino}phenyl)acetamide;

N-(5-isopropyl-1,3-thiazol-2-yl)-2-(4-{methyl[2-(4-morpholinyl)ethyl]amino}phenyl)acetamide;

2-{4-[(2,3-dihydroxypropyl)amino]phenyl}-N-(5-isopropyl-1,3-thiazol-2-yl)acetamide;

2-{4-[(2,3-dihydroxypropyl)(methyl)amino]phenyl}-N-(5-isopropyl-1,3-thiazol-2-yl)acetamide;

2-(4-{[3-(dimethylamino)-2-hydroxypropyl]amino}phenyl)-N-(5-isopropyl-1,3-thiazol-2-yl)acetamide;

2-[4-(1-adamantylamino)phenyl]-N-(5-isopropyl-1,3-thiazol-2-yl)acetamide;

2-{4-[(2-amino-2-oxoethyl)amino]phenyl}-N-(5-isopropyl-1,3-thiazol-2-yl)acetamide;

2-4-{[2-(dimethylamino)-2-oxoethyl]amino}phenyl)-N-(5-isopropyl-1,3-thiazol-2-yl)acetamide;

2-[4-(acetylamino)phenyl]-N-(5-isopropyl-1,3-thiazol-2-yl)acetamide;

N-(4-{2-[(5-isopropyl-1,3-thiazol-2-yl)amino]-2-oxoethyl}phenyl)nicotinamide;

N-(4-{2-[(5-isopropyl-1,3-thiazol-2-yl)amino]-2-oxoethyl}phenyl)-5-methyl-2-thiophenecarboxamide;

N-(4-{2-[(5-isopropyl-1,3-thiazol-2-yl)amino]-2-oxoethyl}phenyl)-5-methyl-2-pyrazinecarboxamide;

N-(4-{2-[(5-isopropyl-1,3-thiazol-2-yl)amino]-2-oxoethyl}phenyl)-5-methyl-4-isoxazolecarboxamide;

N-(4-{2-[(5-isopropyl-1,3-thiazol-2-yl)amino]-2-oxoethyl}phenyl)-3,5-dimethyl-4-isoxazolecarboxamide;

(dimethylamino)-N-(4-{2-[(5-isopropyl-1,3-thiazol-2-yl)amino]-2-oxoethyl}phenyl)benzamide;

4-(acetylamino)-N-(4-{2-[(5-isopropyl-1,3-thiazol-2-yl)amino]-2-oxoethyl}phenyl)benzamide;

4-(dimethylamino)-N-(4-{2-[(5-isopropyl-1,3-thiazol-2-yl)amino]-2-oxoethyl}phenyl)benzamide;

N-(4-{2-[(5-isopropyl-1,3-thiazol-2-yl)amino]-2-oxoethyl}phenyl)-1,3-benzodioxole-5-carboxamide;

4-(aminosulfonyl)-N-(4-{2-[(5-isopropyl-1,3-thiazol-2-yl)amino]-2-oxoethyl}phenyl)benzamide;

2-chloro-2,2-difluoro-N-(4-{2-[(5-isopropyl-1,3-thiazol-2-yl)amino]-2-oxoethyl}phenyl)acetamide;

2-cyano-N-(4-{2-[(5-isopropyl-1,3-thiazol-2-yl)amino]-2-oxoethyl}phenyl)acetamide;

1-acetyl-N-(4-{2-[(5-isopropyl-1,3-thiazol-2-yl)amino]-2-oxoethyl}phenyl)-4-piperidinecarboxamide;

N'1'-(4-{2-[(5-isopropyl-1,3-thiazol-2-yl)amino]-2-oxoethyl}phenyl)succinamide;

N-(4-{2-[(5-isopropyl-1,3-thiazol-2-yl)amino]-2-oxoethyl}phenyl)-2-methoxyacetamide;

3,3,3-trifluoro-N-(4-{2-[(5-isopropyl-1,3-thiazol-2-yl)amino]-2-oxoethyl}phenyl)propanamide;

N-(4-{2-[(5-isopropyl-1,3-thiazol-2-yl)amino]-2-oxoethyl}phenyl)-2-phenylacetamide;

N-(4-{2-[(5-isopropyl-1,3-thiazol-2-yl)amino]-2-oxoethyl}phenyl)-2-methoxy-2-phenylacetamide;

2-[4-(dimethylamino)phenyl]-N-(4-{2-[(5-isopropyl-1,3-thiazol-2-yl)amino]-2-oxoethyl}phenyl)acetamide N-(4-{2-[(5-isopropyl-1,3-thiazol-2-yl)amino]-2-oxoethyl}phenyl)-2-(3-pyridinyl)acetamide;

N-(4-{2-[(5-isopropyl-1,3-thiazol-2-yl)amino]-2-oxoethyl}phenyl)-2-(3-thienyl)acetamide;

N-(4-{2-[(5-isopropyl-1,3-thiazol-2-yl)amino]-2-oxoethyl}phenyl)-2-[5-(1-pyrrolidinyl)-2H-1,2,3,4-tetraazol-2-yl]acetamide;

2-cyclopropyl-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-5-methyl-2-pyrazinecarboxamide;

N-(4-{2-[(5-isopropyl-1,3-thiazol-2-yl)amino]-2-oxoethyl}-1,3-thiazol-2-yl)-2-propynamide;

N-(4-{2-[(5-isopropyl-1,3-thiazol-2-yl)amino]-2-oxoethyl}-1,3-thiazol-2yl)-5-methyl-1,3-oxazole-4-carboxamide;

N-(4-{2-[(5-isopropyl-1,3-thiazol-2-yl)amino]-2-oxoethyl}-1,3-thiazol-2yl)-3,3-dimethylbutanamide;

N-(4-{2-[(5-isopropyl-1,3-thiazol-2-yl)amino]-2-oxoethyl}-1,3-thiazol-2-yl)-3-methyl-2-butenamide;

3-cyclopentyl-N-(4-{2-[(5-isopropyl-1,3-thiazol-2-yl)amino]-2-oxoethyl}-1,3-thiazol-2-yl)propanamide;

N-(4-{2-[(5-isopropyl-1,3-thiazol-2-yl)amino]-2-oxoethyl}-1,3-thiazol-2-yl)-2-(3-thienyl)acetamide;

N-(4-{2-[(5-isopropyl-1,3-thiazol-2-yl)amino]-2-oxoethyl}-1,3-thiazol-2-yl)-2-(3-pyridinyl)acetamide;

2,2,2-trifluoro-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-3-(2-thienyl)propanamide;

N-(4-{2-[(5-isopropyl-1,3-thiazol-2-yl)amino]-2-oxoethyl}-1,3-thiazol-2-yl)-2-(4-pyridinylsulfanyl)acetamide;

N-(4-{2-[(5-isopropyl-1,3-thiazol-2-yl)amino]-2-oxoethyl}-1,3-thiazol-2-yl)-2-(3-pyridinyl)-1,3-thiazole-4-carboxamide;

2-[2-(acetylamino)-1,3-thiazol-4-yl]-N-(5-cyclopropyl-1,3-thiazol-2-yl)acetamide;

2-[2-(acetylamino)-1,3-thiazol-4-yl]-N-{5-[(3-hydroxypropyl)(methyl)amino]-1,3-thiazol-2-yl}acetamide;

2-[2-(acetylamino)-1,3-thiazol-4-yl]-N-{5-[(2-hydroxyethyl)(methyl)amino]-1,3-thiazol-2-yl}acetamide;

2-[4-(dimethylamino)phenyl]-N-{5-[(2-hydroxyethyl)(methyl)amino]-1,3-thiazol-2-yl}acetamide;

2-[4-(dimethylamino)phenyl]-N-{5-[(3-hydroxypropyl)(methyl)amino]-1,3-thiazol-2-yl}acetamide; and N-(5-cyclopropyl-1,3-thiazol-2-yl)-2-[4-(dimethylamino)phenyl]acetamide.

The compounds of formula (I) or (II), and the salts thereof, may be obtained, for example, by a process comprising:

(a) reacting a compound of formula (III):

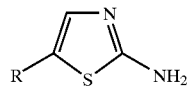

with a compound of formula (IV):

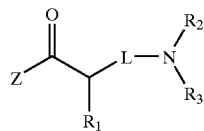

where R, L, $R_1$, $R_2$ and $R_3$ are as above defined, and Z is hydroxy or a suitable leaving group, so as to obtain a compound of formula (I) wherein R, L, $R_1$, $R_2$ and $R_3$ are as defined above; or (b) reacting a compound of formula (I):

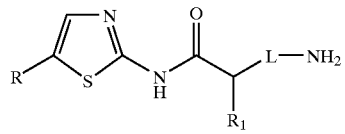

with a compound of formula (V):

$R_4$—COX  (V)

where R, $R_1$, L and $R_4$ are as defined above, and X is hydroxy or a suitable leaving group such as chlorine or bromine, thus obtaining a compound of formula (II), where R, L, $R_1$ and $R_4$ are as defined above; or (c) reacting a compound of the above formula (I), where both or at least one of $R_2$ and $R_3$ is a hydrogen atom, with a compound of formula (VI):

R'Y  (VI)

where R' has the meanings of $R_2$ or $R_3$ but is other than hydrogen, and Y is a suitable leaving group such as bromine, chlorine, mesyl, tosyl, hydroxy, or formyl (CHO), thus obtaining a compound of formula (I) wherein both or at least one of $R_2$ and $R_3$ is other than hydrogen; and, optionally, converting a compound of formula (I) or (II) into another compound of formula (I) or (II), and/or into a salt thereof.

As will be readily appreciated by one skilled in the art, if the compound of formula (I) or (II), prepared according to the above process is obtained as an admixture of isomers, their separation into the single isomers of formula (I) or (II) according to conventional techniques is within the scope of the present invention. Likewise, the conversion into the free compound (I) or (II) of a corresponding salt thereof, according to well-known procedures in the art, is within the scope of the invention.

The above (a), (b), (c) processes are analogy processes which can be carried out according to well-known methods in the art.

The reaction between a compound of formula (III) with a compound of formula (IV) where Z is a hydroxy group, according to process (a), or between a compound of formula (I) wherein both $R_2$ and $R_3$ represent hydrogen atoms with a carboxylic acid of formula (V) wherein X is a hydroxy group, according to process (b), can be carried out in the presence of a coupling agent such as, for instance, carbodiimide, i.e., 1,3-dicyclohexylcarbodiimide, 1,3diisopropylcarbodiimide, or 1-(3-dimethylaminopropyl)-3ethylcarbodiimide, or using a polymer supported carbodiimide, such as N-cyclohexylcarbodiimide, N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10 C. to reflux for a suitable time, i.e., from about 30 min. to about 8 days.

The reaction between a compound of formula (III) and a compound of formula (IV) wherein Z is hydroxy, or between a compound of formula (I) wherein $R_2$ and $R_3$ are hydrogen atoms with a compound of formula (V) wherein X is hydroxy, can be also carried out, for example, by a mixed anhydride method, using an alkyl chloroformate, such as ethyl, iso-butyl, or iso-propyl chloroformate, in the presence of a tertiary base, such as triethylamine, N,N-diisopropylethylamine or pyridine, in a suitable solvent, as, for instance, toluene, dichloromethane, chloroform, tetrahydrofuran, acetonitrile, diethyl ether, 1,4-dioxane, or N,N-dimethylformamide, at a temperature ranging from about −30 C to room temperature.

The reaction between a compound of formula (III) and a carboxylic acid derivative of formula (IV) where Z is suitable leaving group, according to process (a), or between a compound compound of formula (I) wherein both $R_2$ and $R_3$ are hydrogen atoms with a carboxylic acid derivative of formula (V) wherein X is a suitable leaving group, according to process (b), can be carried out in the presence of a tertiary base, such as triethylamine, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about −10 C to reflux.

The reaction between a compound of formula (I) and a compound of formula (VI) wherein Y is a suitable leaving group, according to process (c), can be carried out in the presence of a suitable base, such as potassium carbonate, triethylamine, N,N-diisopropylethylamine or pyridine, in a suitable solvent, such as ethanol, acetonitrile, N,N-dimethylformamide, 1,4-dioxane, or tetrahydrofuran, at a temperature ranging from room temperature to reflux.

The reaction between a compound of formula (I) and a compound of formula (VI) wherein Y is hydroxy, according to process (c), can be carried out under Mitsunobu's conditions, in the presence of triphenylphosphine and diethylazidodicarboxylate, in a suitable solvent, such as tetrahydrofuran, at a temperature ranging from 0 C to room temperature.

The reaction between a compound of formula (I) and a compound of formula (VI) wherein Y is CHO, according to process (c), can be carried out in the presence of conventional reducing agents such as, for instance, sodium borohydride, sodium cyanoborohydride or sodium triacetoxyborohydride, in a suitable solvent, for instance methanol or ethanol, at a temperature ranging from about 0 C to reflux.

Also the optional conversion of a compound of formula (I) or (II) into another compound of formula (I) or (II) can be carried out according to known methods.

As an example, process c) above may be regarded as a possible conversion of a compound of the invention into another compound of the invention.

The optional salification of a compound of formula (I) or (II) or the conversion of a salt into the free compound as well as the separation of a mixture of isomers into the single isomers may be carried out by conventional methods.

The compounds of formula (III), (IV), (V) and (VI), according to the process object of the present invention, are known compounds or can be obtained according to known methods.

A compound of formula (IV) or of formula (V) wherein Z or X are a leaving group as defined above can be obtained according to conventional techniques from the corresponding carboxylic acids of formula (IV) or (V) wherein Z or X is hydroxy.

A compound of formula (III) wherein R is as defined above, can be obtained, for example, by reacting a compound of formula (VII):

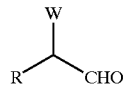

where R is as defined above and W is bromine or chlorine, with thiourea, in a suitable solvent, such as methanol, ethanol, tetrahydrofuran, 1,4-dioxane, or toluene, at a temperature varying between room temperature and reflux, for a suitable time, ranging from about 1 hour to about 24 hours.

The compounds of formula from (IV) to (VII) are, in some cases, commercially available products, or may be prepared by methods well-known in the art.

When preparing the compounds of formula (I) according to the process object of the present invention, optional functional groups within both the starting materials or the intermediates thereof, which could give rise to unwanted side reactions, need to be properly protected according to conventional techniques.

Likewise, the conversion of these latter into the free deprotected compounds may be carried out according to known procedures.

Pharmacology

The compounds of formula (I) or (II), are active as cdk/cyclin inhibitors as they gave positive results when tested according to the following procedure.

The inhibiting activity of putative cdk/cyclin inhibitors and the potency of selected compounds was determined through a method of assay based on the use of the MultiScreen-PH 96 well plate (Millipore), in which a phosphocellulose filter paper was placed at each well bottom allowing binding of positive charged substrate after a washing/filtration step.

When a radioactivity labelled phosphate moiety was transferred by the ser/threo kinase to the filter-bound histone, light emitted was measured in a scintillation counter.

The inhibition assay of cdk2/Cyclin A activity was performed according to the following protocol:

Kinase reaction: 1.5 M histone H1 substrate, 25 M ATP (0.5 uCi P33g-ATP), 100 ng Cyclin A/cdk2 complex, 10 M inhibitor in a final volume of 100 $\mu$L buffer (TRIS HCl 10 mM, pH 7.5, MgCl2 10 mM, 7.5 mM DTT) were added to each well of a 96 U bottom well plate. After 10 min at 37 C incubation, reaction was stopped by 20 $\mu$L EDTA 120 mM.

Capture: 100 l were transferred from each well to MultiScreen plate, to allow substrate binding to phosphocellulose filter. Plates were then washed 3 times with 150 pi/well PBS Ca++/Mg++ free and filtered by MultiScreen filtration system.

Detection: filters were allowed to dry at 37 C, then 100 l/well scintillant were added and 33P labelled histone H1 was detected by radioactivity counting in the Top-Count instrument.

Results: data were analysed and expressed as % inhibition referred to total activity of enzyme (=100%).

All compounds showing inhibition >50% were further analyzed in order to study and define the kinetic-profile of inhibitor through Ki calculation.

The protocol used was the same described above, except for ATP and substrate concentrations. Either the concentration of ATP and histone H1 substrate were varied: 4, 8, 12, 24, 48 AM for ATP (containing proportionally diluted P33g-ATP) and 0.4, 0.8, 1.2, 2.4, 4.8 AM for histone were used in absence and presence of two different, properly chosen inhibitor concentrations.

Experimental data were analysed by the computer program "SigmaPlot" for Ki determination, using a random bireactant system equation:

$$v = \frac{Vmax \ (A)(B)}{\dfrac{aKAKB}{1 + (A) + (B) + (A)(B)}}$$
$$KAKB \quad aKAKB$$

where A=ATP and B=histone H1.

As an example, herewith reported is the inhibiting activity towards the CDk2/cyclin A complex, expressed as IC50 value, of a compound of the invention namely, 2-[2-(acetylamino)1,3-thiazol-4-yl]-N-(5-isopropyl-1,3-thiazol-2-yl)acetamide [0.5 (M)].

In addition, the inhibiting activity of putative cdk/cyclin inhibitors and the potency of selected compounds was determined through a method of assay based on the use of a SPA (Scintillation Proximity Assay) 96 well plate assay. The assay is based on the ability of streptavidin coated SPA beads to capture a biotinylated peptide derived from a phosphorylation site of histone.

When a radioactivity labelled phosphate moiety was transferred by the ser/threo kinase to the biotinylated histone peptide, light emitted was measured in a scintillation counter.

The inhibition assay of cdk5/p25 activity was performed according to the following protocol:

Kinase reaction: 1.0 M biotinylated histone peptide substrate, 0.25 uCi P33g-ATP, 4 nM cdk2/p25 complex, 0–100 M inhibitor in a final volume of 100 l buffer (Hepes 20 mM pH 7.5, MgCl2 15 mM, 1 mM DTT) were added to each well of a 96 U bottom well plate. After 20 min at 37 C incubation, the reaction was stopped by the addition of 500 ug SPA beads in phosphate-buffered saline containing 0.1% Triton X-100, 50 uM ATP and 5 mM EDTA. The beads were allowed to settle, and the radioactivity incorporated in the 33P-labelled peptide was detected in a Top Count scintillation counter.

Results: Data were analyzed and expressed as % Inhibition using the formula:

100X(1−(Unknown−Bkgd)/(Enz. Control−Bkgd))

IC50 values were calculated using a variation of the four parameter logistics equation:

$Y=100/[1+10^{\wedge}((LogEC50-X)*Slope)]$

Where $X$=log(uM) and $Y$=% Inhibition.

The compounds of formula (I) or (II) are therefore useful to restrict the unregulated proliferation of tumor cells, hence in therapy in the treatment of various tumors such as, for instance, carcinomas, e.g., mammary carcinoma, lung carcinoma, bladder carcinoma, colon carcinoma, ovary and endometrial tumors, sarcomas, e.g., soft tissue and bone sarcomas, and the hematological malignancies such as, e.g., leukemias.

In addition, the compounds of formula (I) or (II) are also useful in the treatment of other cell proliferative disorders such as psoriasis, vascular smooth cell proliferation associated with atherosclerosis and postsurgical stenosis and restenosis and in the treatment of Alzheimer's disease.

The compounds of formula (I) or (II) of the present invention, suitable for administration to a mammal, e.g., to humans, can be administered by the usual routes and the dosage level depends upon the age, weight, conditions of the patient and the administration route.

For example, a suitable dosage adopted for oral administration of a compound of formula (I) or (II) may range from about 10 to about 500 mg per dose, from 1 to 5 times daily.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

As an example, the compounds of the invention can be administered in combination with one or more chemotherapeutic agents such as, for instance, taxane, taxane derivatives, encapsulated taxanes, CPT-11, camptothecin derivatives, anthracycline glycosides, e.g., doxorubicin, idarubicin, epirubicin, etoposide, navelbine, vinblastine, carboplatin, cisplatin, estramustine, celecoxib, Sugen SU-5416, Sugen SU-6668, Herceptin, and the like, optionally within liposomal formulations thereof.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The compounds of the invention can be administered in a variety of dosage forms, e.g., orally, in the form of tablets, capsules, sugar or film coated tablets, liquid solutions or suspensions; rectally in the form of suppositories; parentally, e.g., intramuscularly, or by intravenous and/or intrathecal and/or intraspinal injection or infusion.

The present invention also includes pharmaceutical compositions comprising a compound of formula (I) or (II), or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic acid, magnesium or calcium stearate, and/or polyethylene glycols; binding agents, e.g. starches, arabic gum, gelatine, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. The pharmaceutical preparations may be manufactured in known example, by means of mixing, granulating, sugar-coating, or film-coating processes. The liquid dispersions for oral administration manner, for tabletting, may be e.g., syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the present invention.

EXAMPLES

Having generally described this invention, a further understanding can be obtained by reference to certain specific examples which are provided herein for purposes of illustration only and are not intended to be limiting unless otherwise specified.

Example 1

Preparation of 2-amino-5-isopropyl-1,3-thiazole 2 ml (18.6 mmol) of 3-methylbutyraldehyde were dissolved in 15 ml of 1,4dioxane. 40.4 ml (18.6 mmol) of a solution 2% v/v of bromine in 1,4-dioxane was dropped therein at 0 C. The mixture was maintained at room temperature under stirring for 2 hours, then 2.83 g (37.2 mmol) of thiourea and 5 ml of ethanol were added.

After 6 hours at room temperature the solution was evaporated to dryness, the residue was dissolved in CH2Cl2 and the product extracted with 1M hydrochloric acid; the aqueous layer was made basic by using 30% ammonium hydrate and extracted again with CH2Cl2. The organic phase was dried over sodium sulfate and evaporated under vacuum. The residue was chromatographed on a silica gel column, eluting with cyclohexane-ethyl acetate to give 1.1 g (42% yield) of the title compound.

1H-NMR (DMSO-d6) ppm: 6.6 (s, 2H, NH2); 6.58 (s, 1H, thiazole CH); 2.9 (m, 1H, CHMe2); 1.18 (s, 3H, MeCHMe); 1.17 (s, 3H, MeCHMe).

Analogously, starting from the corresponding aldehyde, the following product can be prepared: 2-amino-5-cyclopropyl-1,3-thiazole.

Example 2
Preparation of tert-butyl 4-{2-[(5-isopropyl-1,3-thiazol-2-yl)amino]-2-oxoethyl}-1,3-thiazol-2-ylcarbamate EDCI (20.6 g, 107 mmol) was added to a solution of 2-{2[(tert-butoxycarbonyl)amino]-1,3-thiazol-4-yl}acetic acid (25 g, 97 mmol) in CHCl3 (200 ml) under ice-cooling.

After stirring for 1 hour, a solution of 2-amino-5-isopropyl-1,3-thiazole (13.7 g, 97 mmol) in CHCl3 (150 ml) was added dropwise, and the entire mixture was kept at 0 C for 1 hour, then at room temperature overnight.

The solution was washed with water, 5% citric acid, water, saturated sodium bicarbonate, and brine.

Drying over sodium sulfate and evaporation gave a solid which was chromatographed on silica gel using CH2Cl2:MeOH 95:5 as eluent to give the title compound as a colorless solid (22 g; 59%)

m.p. 196–197 C.

1H-NMR DMSO-d6) ppm: 12 (s, broad, 1H, NH); 11.4 (s, broad, 1H, NHBoc); 7.14 (s, 1H, H4-thiazole); 6.9 (s, 1H, H5-thiazole'); 3.7 (s, 2H, CH2); 3.08 (m, 1H, CHMe2); 1.42 (s, 9H, t-Bu); 1.22 (d, 6H, CHMe2).

Analogously, starting from the corresponding carboxylic acid, the following product can be prepared:

tert-butyl 4-{2-[(5-isopropyl-1,3-thiazol-2-yl)amino]-2-oxoethyl}phenylcarbamate m.p. 179–180 C 1H-NMR (DMSO-d6) ppm: 12.1 (s, broad, 1H, NH); 9.22 (s, broad, 1H, NHBoc); 7.35 (d, 2H, Ph); 7.19 (s, 1H, H4-thiazole); 7.15 (d, 2H, Ph), 3.6 (s, 2H, CH2); 3.08 (m, 1H, CHMe2); 1.43 (s, 9H, t-Bu); 1.11 (d, 6H, CHMe2).

Example 3
Preparation of 2-(2-amino-1,3-thiazol-4-yl)-N-(5-isopropyl-1,3-thiazol-2-yl)acetamide Trifluoroacetic acid (168 ml) was added to a solution of tert-butyl 4-{2-[(5-isopropyl-1,3-thiazol-2-yl)amino]-2-oxoethyl}-1,3-thiazol-2-ylcarbamate (22 g, 57.51 mmol) in CH2Cl2 (750 ml) and anisole (9.33 ml, 86.27 mmol) under ice-cooling.

After stirring for 2 hours at 0 C, the solution was kept at room temperature overnight and then evaporated. The residue was dissolved in CH2Cl2 and the solvent was evaporated (500 ml×3).

The residue was then partitioned between CH2Cl2 and water. The organic layer was further washed with water, saturated sodium bicarbonate and brine.

Drying over sodium sulfate and evaporation gave a solid which was triturated with isopropyl ether/cyclohexane to give the title compound as a beige solid (13 g; 81%)

m.p. 201–203 C.

1H-NMR (DMSO-d6) ppm: 11.98 (s, broad, 1H, NH); 7.13 (s, broad, 1H, NHBoc); 7–6.6 (m, 4, Ph); 5.9 (s, broad, 2H, NH2); 3.55 (s, 2H, CH2); 3.08 (m, 1H, CHMe2); 1.12 (d, 6H, CHMe2).

Analogously, the following products can be prepared:
2-(4-aminophenyl)-N-(5-isopropyl-1,3-thiazol-2-yl)acetamide m.p. 165–166 C.

1H-NMR (DMSO-d6) ppm: 11.98 (s, broad, 1H, NH); 7.13 (s, 1H, H4-thiazole), 7–6.6 (m, 4H, Ph); 5.9 (s, broad, 2H, NH2); 3.55 (s, 2H, CH2); 3.08 (m, 1H, CHMe2); 1,12 (d, 6H, CHMe2);
4-amino-N-(4-{2-[(5-isopropyl-1,3-thiazol-2-yl)amino]-2-oxoethyl}-1,3-thiazol-2-yl)butanamide;
3-amino-N-(4-{2-[(5-isopropyl-1,3-thiazol-2-yl)amino]-2-oxoethyl}-1,3-thiazol-2-yl)propanamide; and
2-amino-N-(4-{2-[(5-isopropyl-1,3-thiazol-2-yl)amino]-2-oxoethyl}-1,3-thiazol-2-yl)acetamide.

Example 4
Preparation of 2-chloro-N-(4-{2-[(5-isopropyl-1,3-thiazol-2-yl)amino-]2-oxoethyl}-1,3-thiazol-2-yl)acetamide EDCI (0.49 g, 2.54 mmol) was added to a solution of 2chloroacetic acid (0.24 g, 2.54 mmol) in CHCl3 (10 ml) under ice-cooling.

After stirring for 1 hour at 0 C, a solution of 2-(2-amino-1,3-thiazol-4-yl)-N-(5-isopropyl-1,3-thiazol-2-yl)acetamide (0.6 g, 2.12 mmol) in CHCl3 (10 ml) was added dropwise, and the entire mixture was kept at 0° C. for 1 hour, then at room temperature overnight.

The solution was washed with water, 5% citric acid, water, saturated sodium bicarbonate, and brine.

Drying over sodium sulfate and evaporation gave a solid which was chromatographed on silica gel using CH2Cl2 and then CH2Cl2:MeOH 99:1 as eluent to give the title compound as a colorless solid (0.49 g; 65%).

m.p. 176–178 C.

1H-NMR (CDCl3) ppm: 11 (s, broad, 2H, 2NH); 7.01 (s, 1H, H4-thiazole); 6.83 (s, 1H, H5-thiazole'); 4.23 (s, 2H, CH2Cl); 3.83 (s, 2H, CH2CO); 3.1 (m, 1H, CHMe2); 1.35 (d, 6H, CHMe2).

Analogously, the following products can be prepared:
2-[2-(acetylamino)-1,3-thiazol-4-yl]-N-(5-isopropyl-1,3-thiazol-2-yl)acetamide m.p. 174–176C.

1H-NMR (DMSO-d6) ppm: 12.1 (2s, broad, 2H, 2NH); 7.15 (s, 1H, H4-thiazole); 6.93 (s, 1H, H5-thiazole'); 3.77 (s, 2H, CH2); 3.3 (s, 3H, CH3); 3.1 (m, 1H, CHMe2); 1.22 (d, 6H, CHMe2);
4-chloro-N-(4-{2-[(5-isopropyl-1,3-thiazol-2-yl)amino]-2-oxoethyl}-1,3-thiazol-2-yl)butanamide m.p. 170–172 C.

1H-NMR (DMSO-d6) ppm: 12.15 (s, broad, 1H, NH); 12.05 (s, broad, 1H, NH); 7.12 (s, 1H, H4-thiazole); 6.95 (s, 1H, H5-thiazole'); 3.76 (s, 2H, CH2CO); 3.62 (t, 2H, CH2CH2CH2Cl); 3.08 (m, 1H, CHMe2); 2.55 (t, 2H, CH2CH2CH2Cl); 2 (tt, 2H, CH2CH2CH2Cl); 1.1 (d, 6H, CHMe2).
N-(4-{2-[(5-isopropyl-1,3-thiazol-2-yl)amino]-2-oxoethyl}-1,3-thiazol-2-yl)-2-methoxyacetamide m.p. 147–149 C.

1H-NMR (DMSO-d6) ppm: 12.03 (s, broad, 1H, NH); 7.11 (s, 1H, H4-thiazole); 6.98 (s, 1H, H5-thiazole'); 4.09 (s, 3H, OMe); 3.79 (s, 2H, CH2); 3.1 (m, 1H, CHMe2); 1.21 (d, 6H, CHMe2);
3,3,3-trifluoro-N-(4-{2-[(5-isopropyl-1,3-thiazol-2-yl)amino]-2-oxoethyl}-1,3-thiazol-2-yl)propanamide m.p. 214–216 C.

1H-NMR (DMSO-d6) ppm: 12.5 (s, broad, 1H, NH); 12.1 (s, broad, 1H, NH); 7.15 (s, 1H, H4-thiazole); 7.02 (s, 1H, H5-thiazole'); 3.79 (s, 2H, CH2); 3.6 (q, 2H, CH2CF3); 3.1 (m, 1H, CHMe2); 1.11 (d, 6H, CHMe2); 2-[4-(dimethylamino)phenyl]-N-(5-isopropyl-1,3-thiazol-2-yl)-acetamide;

m.p. 136–137 C.

1H-NMR 1H-NMR (DMSO-d6) ppm: 12 (s, broad, 1H, NH); 7.11 (s, 1H, H4-thiazole); 7.1 (d, 2H, Ph); 6.65 (d, 2H, Ph); 3.55 (s, 2H, CH2); 3.1 (m, 1H, CHMe2); 2.82 (s, 6H, NMe2); 1.21 (d, 6H, CHMe2);
2-[4-(acetylamino)phenyl]-N-(5-isopropyl-1,3-thiazol-2-yl)-acetamide m.p. 186–187° C.

1H-NMR (DMSO-d6) ppm: 12.09 (s, broad, 1H, NH); 9.9 (s, broad, 1H, NH); 7.6–7.2 (m, 4H, Ph); 7.15 (s, 1H, H4thiazole); 3.62 (s, 2H, CH2), 3.08 (m, 1H, CHMe2); 2-(s, 3H, CH3); 1.21 (d, 6H, CHMe2);
tert-butyl 2-[(4-{2-[(5-isopropyl-1,3-thiazol-2-yl)amino]2-oxoethyl}-1,3-thiazol-2-yl)amino]-2-oxoethylcarbamate;
tert-butyl 3-[(4-{2-[(5-isopropyl-1,3-thiazol-2-yl)amino]-2-oxoethyl}-1,3-thiazol-2-yl)amino]-3-oxopropylcarbamate; and tert-butyl 4-[(4-{2-[(5-isopropyl-1,3-thiazol-2-yl)amino]2-oxoethyl}-1,3-thiazol-2-yl)amino]-4-oxobutylcarbamate;
2-[4-(dimethylamino)phenyl]-N-(5-nitro-1,3-thiazol-2-yl)acetamide;
2-[2-(acetylamino)-1,3-thiazol-4-yl]-N-(5-nitro-1,3-thiazol-2-yl)acetamide; and
N-(5cyclopropyl-1,3-thiazol-2-yl)-2-[4-(dimethylamino)phenyl]acetamide.

Example 5

Preparation of N-(4-{2-[(5-isopropyl-1,3-thiazol-2-yl)amino]-2-oxoethyl}-1,3-thiazol-2-yl)-2-methylpropanamide To a solution of isobutyrric acid (49 l, 0.53 mmol) in CH2Cl2 (1.5 ml), N-cyclohexylcarbodiimide, N'-methyl polystyrene (0.4 g, loading 2 mmol/g, 0.798 mmol), Nhydroxybenzotriazole (0.072 g, 0.53 mmol) and a solution of 2-(2-amino-1,3-thiazol-4-yl)-N-(5-isopropyl-1,3-thiazol-2-yl)acetamide (0.075 g, 0.266 mmol) in CH2Cl2/DMF (0.4 ml/0.6 ml) were added. The reaction mixture was maintained under stirring at room temperature for about 8 days. After this time, PS-Trisamine (0.44 g, loading 3.62 mmol/g, 1.596 mmol) was added, stirring was continued for about 6 hours and then the mixture was filtered. The resin was washed with CH2Cl2 (1 ml×5), the organic layers were combined and evaporated to dryness to give, after trituration with diisopropyl ether the title compound.

Analogously, starting from the corresponding carboxylic acids, the following compounds can be prepared:
N-(4-{2-[(5-isopropyl-1,3-thiazol-2-yl)amino]-2-oxoethyl}-1,3-thiazol-2-yl)acrylamide;
N-(4-{2-[(5-isopropyl-1,3-thiazol-2-yl)amino]-2-oxoethyl}-1,3-thiazol-2-yl)-2-naphthamide;
N-(4-{2-[(5-isopropyl-1,3-thiazol-2-yl)amino]-2-oxoethyl}-1,3-thiazol-2-yl)benzamide;
N-(4-{2-[(5-isopropyl-1,3-thiazol-2-yl)amino]-2-oxoethyl}-1,3-thiazol-2-yl)-2-phenylacetamide;
N-(4-{2-[(5-isopropyl-1,3-thiazol-2-yl)amino]-2-oxoethyl}-1,3-thiazol-2-yl)-2-(3-pyridinyl)acetamide;
2,2,3,3,3-pentafluoro-N-(4-{2-[(5-isopropyl-1,3-thiazol-2yl)amino]-2-oxoethyl}-1,3 -thiazol-2-yl)propanamide;
2-fluoro-N-(4-{2-[(5-isopropyl-1,3-thiazol-2-yl)amino]-2-oxoethyl}-1,3-thiazol-2-yl)acetamide;
2-cyano-N-(4-{2-[(5-isopropyl-1,3-thiazol-2-yl)amino]-2-oxoethyl}-1,3-thiazol-2-yl)acetamide;
N-(4-{2-[(5-isopropyl-1,3-thiazol-2-yl)amino]-2-oxoethyl}-1,3-thiazol-2-yl)-2-(4-methyl-1-piperazinyl)acetamide;
2-(4benzyl-1-piperazinyl)-N-(4-{2-[(5-isopropyl-1,3-thiazol-2-yl)amino]-2-oxoethyl}-1,3-thiazol-2-yl)acetamide;
N-(4-{2-[(5-isopropyl-1,3-thiazol-2-yl)amino]-2-oxoethyl}-1,3-thiazol-2-yl)-2-(1-piperidinyl)acetamide;
2-[4-(dimethylamino)phenyl)-N-(4-{2-[(5-isopropyl-1,3-thiazol-2-yl)amino]-2-oxoethyl}-1,3-thiazol-2-yl)acetamide;
N-(4-{2-[(5-isopropyl-1,3-thiazol-2-yl)amino]-2-oxoethyl}-1,3-thiazol-2-yl)-2-(1H-1,2,3,4-tetrazol-1-yl)acetamide;
N-(4-{2-[(5-isopropyl-1,3-thiazol-2-yl)amino]-2-oxoethyl}-1,3-thiazol-2-yl)-5-oxo-2-pyrrolidinecarboxamide;
N'1'-(4-{2-[(5-isopropyl-1,3-thiazol-2-yl)amino]-2-oxoethyl}-1,3-thiazol-2-yl)malonamide;
N'1'-(4-{2-[(5-isopropyl-1,3-thiazol-2-yl)amino]-2-oxoethyl}-1,3-thiazol-2-yl)succinamide;
3-(1H-benzimidazol-2-yl)-N-(4-{2-[(5-isopropyl-1,3-thiazol-2-yl)amino]-2-oxoethyl}-1,3-thiazol-2-yl)propanamide; and
1-acetyl-N-(4-{2-[(5-isopropyl-1,3-thiazol-2-yl)amino]-2-oxoethyl}-1,3-thiazol-2-yl)-4-piperidinecarboxamide;
2-cyclopropyl-N-(4-{2-[(5-isopropyl-1,3-thiazol-2-yl)amino]-2-oxoethyl}-1,3-thiazol-2-yl)acetamide;
N-(4-{2-[(5-isopropyl-1,3-thiazol-2-yl)amino]-2-oxoethyl}-1,3-thiazol-2-yl)-5-methyl-2-pyrazinecarboxamide;
N-(4-{2-[(5-isopropyl-1,3-thiazol-2-yl)amino]-2-oxoethyl}-1,3-thiazol-2-yl)-2-propynamide;
N-(4-{2-[(5-isopropyl-1,3-thiazol-2-yl)amino]-2-oxoethyl}-1,3-thiazol-2-yl)-5-methyl-1,3-oxazole-4-carboxamide;
N-(4-{2-[(5-isopropyl-1,3-thiazol-2-yl)amino]-2-oxoethyl}-1,3-thiazol-2-yl)-3,3-dimethylbutanamide;
N-(4-{2-[(5-isopropyl-1,3-thiazol-2-yl)amino]-2-oxoethyl}-1,3-thiazol-2-yl)-3-methyl-2-butenamide;
3-cyclopentyl-N-(4-{2-[(5-isopropyl-1,3-thiazol-2-yl)amino]-2-oxoethyl}-1,3-thiazol-2-yl)propanamide;
N-(4-{2-[(5-isopropyl-1,3-thiazol-2-yl)amino]-2-oxoethyl}-1,3-thiazol-2-yl)-2-(3-thienyl)acetamide;
N-(4-{2-[(5-isopropyl-1,3-thiazol-2-yl)amino]-2-oxoethyl}-1,3-thiazol-2-yl)-2-(3-pyridinyl)acetamide;
2,2,2-trifluoro-N-(4-{2-[(5-isopropyl-1,3-thiazol-2-yl)amino]-2-oxoethyl}-1,3-thiazol-2-yl)acetamide;
N-(4-{2-[(5-isopropyl-1,3-thiazol-2-yl)amino]-2-oxoethyl}-1,3-thiazol-2-yl)-3-(2-thienyl)propanamide;
N-(4-{2-[(5-isopropyl-1,3-thiazol-2-yl)amino]-2-oxoethyl}-1,3-thiazol-2-yl)-2-(4-pyridinylsulfanyl)acetamide;
N-(4-{2-[(5-isopropyl-1,3-thiazol-2-yl)amino]-2-oxoethyl}-1,3-thiazol-2-yl)-2-(3-pyridinyl)-1,3-thiazole-4 carboxamide;
2-[2-(acetylamino)-1,3-thiazol-4-yl]-N-(5-cyclopropyl-1,3-thiazol-2-yl)acetamide;

Example 6

Preparation of ethyl 2-[(4-{2-[(5-isopropyl-1,3-thiazol-2-yl)amino]-2-oxoethyl}-1,3-thiazol-2-yl)amino]-2-oxoacetate A solution of ethyl oxalyl chloride (1.2 ml, 10.6 mmol) in CHCl3 (3 ml) was added dropwise to a solution of 2-(2amino-1,3-thiazol-4-yl)-N-(5-isopropyl-1,3-thiazol-2-yl)acetamide (2.5 g, 8.85 mmol) and triethylamine (1.85 ml, 13.28 mmol) in CHCl3/DMF (50 ml/15 ml), while cooling at 0 C. The reaction mixture was stirred for about 1 hour at 0 C and at room temperature overnight, then washed with water, 5% citric acid, saturated sodium bicarbonate, brine, dried over sodium sulfate and evaporated to dryness to give the title compound which was used without any further purification (1.2 g).

Analogously, starting from the corresponding acid chloride, the following compounds were prepared and used as crude materials:
ethyl 3-[(4-{2-[(5-isopropyl-1,3-thiazol-2-yl)-amino]-2-oxoethyl}-1,3-thiazol-2-yl)amino]-3-oxopropanoate; and
ethyl 4-[(4-{2-[(5-isopropyl-1,3-thiazol-2-yl)amino]-2-oxoethyl}-1,3-thiazol-2-yl)amino]-4-oxobutanoate.

Example 7

Preparation of 2-[(4-{2-[(5-isopropyl-1,3-thiazol-2-yl)amino]-2-oxoethyl}-1,3-thiazol-2-yl)amino]-2-oxoacetic-acid The crude material obtained in Example 6 (0.5 g; 1.31 mmol) was dissolved in 1,4-dioxane/methanol (10 ml/5 ml) and treated with 1N NaOH (1.5 ml, 1.5 mmol), temperature for about 48 hours. 1N HCl (1.5 ml) while cooling in an ice bath and the resulting filtered, washed with methanol and dried to yield compound as a colorless solid (0.25 g, 54%).
m.p. 214–215 C.

1H-NMR (DMSO-d6) ppm: 12.65 (s, broad, 1H, NH); 12.1 (s, broad, 1H, NH); 7.15 (s, 1H, H4-thiazole); 7.1 (s, 1H, H5 thiazole'); 4.8 (s, 2H, CH2); 3.1 (m, 1H, CHMe2); 1.21 (d, 6H, CHMe2);

Analogously, the following compounds can be prepared:

N-(4-{2-[(5-isopropyl-1,3-thiazol-2-yl)amino]-2-oxoethyl}-1,3-thiazol-2-yl)-3-oxo-beta-alanine
m.p. 196–188C.

1H-NMR (DMSO-d6) ppm: 12.77 (s, broad, 1H, COOH); 12.22 (s, broad, 1H, NH); 12.05 (s, broad, 1H, NH); 7.25 (s, 1H, H4-thiazole); 6.98 (s, 1H, H5-thiazole'); 3.8 (s, 2H, CH2COOH); 3.42 (s, 2H, CH2); 3.2 (m, 1H, CHMe2); 1.22 (d, 6H, CHMe2); and 4-[(4-{2-[(5-isopropyl-1,3-thiazol-2-yl)amino]-2-oxoethyl}-1,3-thiazol-2-yl)amino]-4-oxobutanoic acid.

Example 8
Preparation of 2-[2-(glycoloylamino)-1,3-thiazol-4-yl]-N-(5-isopropyl-1,3-thiazol-2-yl)acetamide The crude material obtained in Example 6 (0.7 g, 1.8 mmol) was partially dissolved in diethyl ether/tetrahydrofuran (65 ml/30 ml) and treated with methanol (0.13 ml, 3.15 mmol) and LiBH4 (0.07 g, 3.15 mmol). The reaction mixture was stirred at 45 C for about 20 minutes, tetrahydrofuran (20 ml) was added and, after 1 more hour, an additional amount of methanol (0.03 ml) and LiBH4 (0.018 g) were added. Stirring was continued for 1 hour, the suspension was quenched with 1N HCl, diluted with water and extracted with CH2Cl2. The organic layer was washed with 1N HCl, brine, dried and evaporated. The residue was triturated with diisopropyl ether and subsequently chromatographed on silica gel, using CHCl3:MeOH:30% N40H 97:3:0.3 as eluent, to give the title compound as a colorless solid (0.154 g, 28%).
m.p. 173–175 C.

1H-NMR (CDCl3) ppm: 6.95 (s, 1H, H4-thiazole); 6.7 (s, 1H, H5-thiazole'); 4.26 (s, 2H, CH2OH); 3.8 (s, 2H, CH2); 3.1 (m, 1H, CHMe2); 1.21 (d, 6H, CHMe2);

Analogously, starting from the corresponding ester derivatives, the following compounds can be prepared:

3-hydroxy-N-(4-{2-[(5-isopropyl-1,3-thiazol-2-yl)amino]-2-oxoethyl}-1,3-thiazol-2-yl)propanamide; and 4-hydroxy-N-(4-{2-[(5-isopropyl-1,3-thiazol-2-yl)amino]-2-oxoethyl}-1,3-thiazol-2-yl)butanamide.

Example 9
Preparation of 2-(dimethylamino)-N-(4-{2-[(5-isopropyl-1,3-thiazol-2-yl)amino]-2-oxoethyl}-1,3-thiazol-2-yl)acetamide A mixture of 2-chloro-N-(4-{2-[(5-isopropyl-1,3-thiazol-2-yl)amino]-2-oxoethyl}-1,3-thiazol-2-yl)acetamide (0.5 g, 1.4 mmol), 2M dimethylamine in methanol (3.5 ml, 7 mmol) and potassium iodide (0.116 g, 0.7 mmol) was refluxed for about 6 hours. After cooling, the solution was diluted with water, acidified with 1N HCl and extracted with diethyl ether to eliminate the unreacted products. The aqueous solution was then basified with 1N NaOH and extracted with diethyl ether. The organic layer was dried over sodium sulfate and evaporated. The residue was purified by chromatography on silica gel, using CH2Cl2:MeOH 97:3 and then 95:5 as eluent. The title compound was obtained in 20% yield (0.1 g) as a light yellow solid.
m.p. 70–71 C.

1H-NMR (DMSO-d6) ppm: 12.1 (s, broad, 1H, NH); 11.8 (s, broad, 1H, NH); 7.17 (s, 1H, H4-thiazole); 6.95 (s, 1H, H5thiazole'); 3.75 (s, 2H, CH2NMe2); 3.17 (s, 2H, CH2); 3.1 (m, 1H, CHMe2); 2.12 (s, 6H, NMe2); 1.22 (d, 6H, CHMe2);

Example 10
Preparation of 2-(2-{[2-(dimethylamino)-2-oxoethyliamino}-1,3-thiazol-4-yl)-N-(5-isopropyl-1,3-thiazol-2-yl)acetamide A mixture of 2-(2-amino-1,3-thiazol-4-yl)-N-(5-isopropyl-1,3-thiazol-2-yl)acetamide (0.6 g, 2.12 mmol), 2-chloroN,N-dimethylacetamide (0.27 ml, 1.96 mmol) and dry potassium carbonate (0.54 g, 3.92 mmol) in dry DMF (5 ml) was stirred at 60 C for about 4 hours. After cooling, the solution was diluted with water, extracted with CHCl3. The organic layer was washed with brine, dried and evaporated. The residue was purified by chromatography on silica gel, using CH2Cl2 followed by CH2Cl2:MeOH 95:5 as eluent. The title compound was obtained in 62% yield (0.5 g) as a colorless solid. m.p. 211–213 C 1H-NMR (DMSO-d6) ppm: 7.02 (s, 1H, H4-thiazole); 6.75 (s, 1H, H5-thiazole'); 5 (s, 2H, NHCH2); 3.43 (s, 2H, NHCOCH2); 3.55 (s, 2H, CH2); 3.1 (s, 3H, NMe); 2.98 (m, 1H, CHMe2); 2.82 (s, 3H, NMe); 1.2 (d, 6H, CHMe2);

Analogously the following products can be prepared starting from the corresponding alkyl halide:

2-{2-[2-amino-2-oxoethyl)amino]-1,3-thiazol-4-yl}-N-(5-isopropyl-1,3-thiazol-2-yl)acetamide
m.p. 172–174 C.

1H-NMR (DMSO-d6) ppm: 7.6 (s, broad, 1H, NHCO); 7.2 (s, broad, 1H, NH); 7.09 (s, 1H, H4-thiazole); 6.72 (s, 1H, H5-thiazole'); 4.7 (s, 2H, NHCH2); 3.45 (s, 2H, NHCOCH2); 2.95 (m, 1H, CHMe2); 1.2 (d, 6H, CHMe2);

N-(5-isopropyl-1,3-thiazol-2-yl)-2-(2-{[2-(4-morpholinyl)ethyl]amino}-1,3-thiazol-4-yl)acetamide;

2-{2-[(2,3-dihydroxypropyl)amino]-1,3-thiazol-4-yl}-N-(5-isopropyl-1,3-thiazol-2-yl)acetamide, 2-[2-(1-adamantylamino)-1,3-thiazol-4-yl]-N-(5-isopropyl-1,3-thiazol-2-yl)acetamide;

N-(5-isopropyl-1,3-thiazol-2-yl)2-(2-{[2-(4-methyl-1-piperazinyl)ethyl]amino}-1,3-thiazol-4-yl)acetamide;

2-(2-{[3-(dimethylamino)-2-hydroxypropyl]amino}-1,3-thiazol-4-yl)-N-(5-isopropyl-1,3-thiazol-2-yl)acetamide;

N-(5-isopropyl-1,3-thiazol-2-yl)-2-[4-(4-methyl-1-piperazinyl)phenyl]acetamide;

N-(5-isopropyl-1,3-thiazol-2-yl)-2-[4-(4-morpholinyl)phenyl]acetamide;

N-(5-isopropyl-1,3-thiazol-2-yl)-2-[4-(1-pyrrolidinyl)phenyl]acetamide;

N-(5-isopropyl-1,3-thiazol-2-yl)-2-(4-{[2-(4-methyl-1-piperazinyl)ethyl]amino}phenyl)acetamide;

N-(5-isopropyl-1,3-thiazol-2-yl)-2-(4-{[2-(4morpholinyl)ethyl]amino}phenyl)acetamide;

2-{4-[(2,3-dihydroxypropyl)amino]phenyl}-N-(5-isopropyl-1,3-thiazol-2-yl)acetamide;

2-(4-{[3-(dimethylamino)-2-hydroxypropyl]amino}phenyl)-N-(5-isopropyl-1,3-thiazol-2-yl)acetamide;

2-[4-(1-adamantylamino)phenyl]-N-(5-isopropyl-1,3-thiazol-2-yl)acetamide;

2-{4-[(2-amino-2-oxoethyl)amino]phenyl}-N-(5-isopropyl-1,3-thiazol-2-yl)acetamide;

2-(4-{[2-(dimethylamino)-2-oxoethyl]amino}phenyl)-N-(5-isopropyl-1,3-thiazol-2-yl)acetamide;

Example 11
Preparation of N-(5-isopropyl-1,3-thiazol-2-yl)-2-(2-{methyl[2-(4-methyl-1-piperazinyl)ethyl]amino}-1,3-thiazol-4-yl)acetamide N-(5-isopropyl-1,3-thiazol-2-yl)-2-(2-{[2-(4-methyl-1piperazinyl)ethyl]amino}-1,3-thiazol-4-yl)acetamide (1 g, 2.45 mmol) and 40% formaldehyde in water (0.17 ml, 2.45 mmol) were mixed in CHCl3 (10 ml) and then treated with sodium triacetoxyborohydride (0.727 g, 3.43 mmol). The mixture was stirred at room temperature under a nitrogen atmosphere for 5 hours. The reaction mixture was quenched by adding aqueous saturated sodium bicarbonate and the product was extracted with CHCl3. The organic layer was washed with brine, dried and evaporated. The title compound was obtained after chromatographic purification in 75% yield.

Analogously, the following products can be prepared:
2-{2-[(2,3-dihydroxypropyl)(methyl)amino]-1,3-thiazol-4-yl}-N-(5-isopropyl-1,3-thiazol-2-yl)acetamide,
N-(5-isopropyl-1,3-thiazol-2-yl)-2-(2-{methyl[2-(4morpholinyl)ethyl]amino}-1,3-thiazol-4-yl)acetamide;
N-(5-isopropyl-1,3-thiazol-2-yl)-2-(4-{methyl[2-(4-morpholinyl)ethyl]amino}phenyl)acetamide;
N-(5-isopropyl-1,3-thiazol-2-yl)-2-(4-{methyl-1-piperazinyl)ethyl]amino}phenyl)acetamide;
2-{4-[(2,3-dihydroxypropyl)(methyl)amino]phenyl}-N-(5-isopropyl-1,3-thiazol-2-yl)acetamide;
3-[[2-({2-[4-(dimethylamino)phenyl]acetyl}amino)-1,3-thiazol-5-yl](methyl)amino]propyl acetate;
2-[[2-({2-[4-(dimethylamino)phenyl]acetyl}amino)-1,3-thiazol-5-yl](methyl)amino]ethyl acetate;
2-[[2-({2-[2-(acetylamino)-1,3-thiazol-4-yl]acetyl}amino)-1,3-thiazol-5-yl](methyl)amino]ethyl acetate; and
3-[[2-({2-[2-(acetylamino)-1,3-thiazol-4-yl]acetyl}amino)-1,3-thiazol-5-yl](methyl)amino]propyl acetate.

Example 12
Preparation of N-(4-{2-[(5-isopropyl-1,3-thiazol-2-yl)amino]-2-oxoethyl}phenyl)-2-methoxyacetamide To a solution of 2-methoxyacetic acid (41 μl, 0.53 mmol) in CH2Cl2 (1.5 ml), N-cyclohexylcarbodiimide, N'-methyl polystyrene (0.53 g, loading 2 mmol/g, 1.064 mmol), previously washed with CH2Cl2 (5 ml×3), 4-DMAP (0.032 g, 0.266 mmol) and a solution of 2-(4-aminophenyl)-N-(5-isopropyl-1,3-thiazol-2-yl)acetamide (0.076 g, 0.266 mmol) in CH2Cl2/DMF (0.4 ml/10.6 ml) were added. The reaction mixture was maintained under stirring at room temperature for about 72 hours the resin was filtered, washed with CH2Cl2 (10 ml×3), the filtrated combined, washed with water, 5% hydrochloric acid, water, saturated sodium bicarbonate and water, dried and evaporated.

Analogously, starting from the corresponding carboxylic acids, the following compounds can be prepared:
N-(4-{2-[(5-isopropyl-1,3-thiazol-2-yl)amino]-2-oxoethyl}phenyl)nicotinamide;
N-(4-{2-[(5-isopropyl-1,3-thiazol-2-yl)amino]-2-oxoethyl}phenyl)-5-methyl-2-thiophenecarboxamide;
N-(4-{2-[(5-isopropyl-1,3-thiazol-2-yl)amino]-2-oxoethyl}phenyl)-5-methyl-2-pyrazinecarboxamide;
N-(4-{2-[(5-isopropyl-1,3-thiazol-2-yl)amino]-2-oxoethyl}phenyl)-5-methyl-4-isoxazolecarboxamide;
N-(4-{2-[(5-isopropyl-1,3-thiazol-2-yl)amino]-2-oxoethyl}phenyl)-3,5-dimethyl-4-isoxazolecarboxamide;
(dimethylamino)-N-(4-{2-[(5-isopropyl-1,3-thiazol-2-yl)amino]-2-oxoethyl}phenyl)benzamide;
4-(acetylamino)-N-(4-{2-[(5-isopropyl-1,3-thiazol-2-yl)amino]-2-oxoethyl}phenyl)benzamide;
4-(dimethylamino)-N-(4-{2-[(5-isopropyl-1,3-thiazol-2-yl)amino]-2-oxoethyl}phenyl)benzamide;
N-(4-{2-[(5-isopropyl-1,3-thiazol-2-yl)amino]-2-oxoethyl}phenyl)-1,3-benzodioxole-5-carboxamide;
4-(aminosulfonyl)-N-(4-{2-[(5-isopropyl-1,3-thiazol-2-yl)amino]-2-oxoethyl}phenyl)benzamide;
2-chloro-2,2-difluoro-N-(4-{2-[(5-isopropyl-1,3-thiazol-2-yl)amino]-2-oxoethyl}phenyl)acetamide;
2-cyano-N-(4-{2-[(5-isopropyl-1,3-thiazol-2-yl)amino]-2-oxoethyl}phenyl)acetamide;
1-acetyl-N-(4-{2-[(5-isopropyl-1,3-thiazol-2-yl)amino]-2-oxoethyl}phenyl)-4-piperidinecarboxamide;
N'1'-(4-{2-[(5-isopropyl-1,3-thiazol-2-yl)amino]-2-oxoethyl}phenyl)succinamide;
3,3,3-trifluoro-N-(4-{2-[(5-isopropyl-1,3-thiazol-2-yl)amino]-2-oxoethyl}phenyl)propanamide;
N-(4-{2-[(5-isopropyl-1,3-thiazol-2-yl)amino]-2-oxoethyl}phenyl)-2-phenylacetamide;
N-(4-{2-[(5-isopropyl-1,3-thiazol-2-yl)amino]-2-oxoethyl}phenyl)-2-methoxy-2-phenylacetamide;
2-[4-(dimethylamino)phenyl]-N-(4-{2-[(5-isopropyl-1,3-thiazol-2-yl)amino]-2-oxoethyl}phenyl)acetamide;
N-(4-{2-[(5-isopropyl-1,3-thiazol-2-yl)amino]-2-oxoethyl}phenyl)-2-(3-pyridinyl)acetamide
N-(4-{2-[(5-isopropyl-1,3-thiazol-2-yl)amino]-2oxoethyl}phenyl)-2-(3-thienyl)acetamide;
N-(4-{2-[(5-isopropyl-1,3-thiazol-2-yl)amino]-2oxoethyl}phenyl)-2-[5-(1-pyrrolidinyl)-2H-1,2,3,4-tetraazol-2-yl]acetamide.

Example 13
Preparation of N-(5-isopropyl-1,3-thiazol-2-yl)-2-[2-(2-oxo-1-pyrrolidinyl)-1,3-thiazol-4-yl]acetamide A mixture of 2.8 g (0.01 mol) of 2-(2-amino-1,3-thiazol-4-yl)-N-(5-isopropyl-1,3-thiazol-2-yl)acetamide, 4.84 g (0.02 mol) of ethyl-iodobutyrate and 2.76 g (0.02 mol) of potassium carbonate in 50 ml of absolute ethanol was stirred under reflux for 5 hours. The mixture was cooled and filtered, and the salts were washed with two 20 ml portions of ethanol. The ethanol was removed at reduced pressure and the residue was dissolved in 100 ml of CH2Cl2. The solution was washed with 30 ml of water, dried, and the solvent was evaporated. The residue was purified by chromatography on silica gel, using CH2Cl2:MeOH 95:5 as eluent, to give the title compound in 30% yield (1.05 g).

Example 14
Preparation of 1-(2,2-diethoxyethyl)cyclopropane

Diazomethane (6.17 g, 147 mmol) was added dropwise to 3.02 g (21 mmol) of 3-butenal diethyl acetal in 10 ml of dry ether with intensive stirring at 0 C. Then 70 mg (0.312 mmol) of palladium (II) acetate in 50 ml of dry ether was added all at once. Then stirring at 0 C continued until the evolution of N2 ceased (10 min.). The ether was distilled off to the reduced volume of the reaction mixture ca 10 ml. The precipitate was filtered off on a fritted glass funnel and the filtrate evaporated. The crude product (2.57 g) contained 97% of the title compound (GC) and was used without further purification.

Example 15
Preparation of 2-cyclopropylacetaldehyde 1-(2,2-Diethoxyethyl)cyclopropane (2.57 g, 16 mmol) was suspended in aq. HCl (0.1 M, 120 ml) and stirred at room temp., for 30 h, after which TLC indicated complete conversion to product yielding a turbid solution. The reaction mixture was then extracted with ether. The ethereal solution was washed with water, dried, and the solvent was evaporated. The residue was purified by chromatography on silica gel, using petroleum ether: ethyl acetate 95:5 as eluent, to give the title compound as an oil (1.07 g, 80%).

Example 16
Preparation of 2-[2-(acethylamino)-1,3-thiazol-4-yl]-N-(5-amino-1,3-thiazol-2-yl)acetamide A solution of 2-[2-(acethylamino)-1,3-thiazol-4-yl]-N-(5-nitro-1,3-thiazol-2-yl)acetamide (1 g, 3.23 mmol) in ethanol (150 ml) was hydrogenated in the presence of 10% Pd/C (0.1 g, 10% w/w) at room temperature for about 5 hours. The reaction mixture was filtered and evaporated. The residue was triturated with diisopropyl ether to give the title compound in 89% yield (0.8 g)

Analogously, the following compound can be prepared, starting from the corresponding nitro derivative:

2-[4-(dimethylamino)phenyl]-N-(5-amino-1,3-thiazol-2-yl)acetamide.

Example 17

Preparation of 3-{[2-({2-[2-(acetylamino)-1,3-thiazol-4-yl]acetyl}amino)-1,3-thiazol-5-yl]amino}propyl acetate A solution of 2-[2-(acethylamino)-1,3-thiazol-4-yl]-N-(5amino-1,3-thiazol-2-yl)acetamide (0.5 g, 1.79 mmol), 3bromopropyl acetate (0.4 g, 2.15 mmol), 2,6-lutidine (0.25 ml, 2.15 mmol) in DMF (10 ml) was heated at 70 C for about 72 hours. The reaction mixture was diluted with water, acidified with 0.5N HCl and extracted with CH2Cl2. The aqueous layer was brought to pH 7/8 with 0.5N NaOH and extracted with CH2Cl2. The organic layer was washed with brine, dried and evaporated. The residue was chromatographed on silica gel, using CH2Cl2:MeOH 95:5 as eluent, to give the title compound in 45% yield.

Analogously, the following compounds can be prepared:
2-{[2-({2-[2-(acetylamino)-1,3-thiazol-4-yl]acetyl}amino)-1,3-thiazol-5-yl]amino}ethyl acetate,
2-{[2-({2-[4-(dimethylamino)phenyl]acetyl}amino)-1,3-thiazol-5-yl]amino}ethyl acetate; and
3-{[2-({2-[4-(dimethylamino)phenyl]acetyl}amino)-1,3-thiazol-5-yl]amino}propyl acetate Example 18

Preparation of. 2-[2-(acetylamino)-1,3-thiazol-4-yl]-N-{5-[(3-hydroxypropyl)(methyl)amino]-1,3-thiazol-2-yl}acetamide 3-[[2-({2-[2-(acetylamino)-1,3-thiazol-4-yl]acetyl}amino)-1,3-thiazol-5-yl](methyl)amino]propyl acetate (0.5 g, 1.27 mmol) was dissolved in methanol (30 ml) and treated with 1N NaOH (1.4 ml, 1.4 mmol) at 0 C for about 24 hours. The solvent was evaporated and the residue was dissolved in CH2Cl2/water. The organic layer was washed with water, brine, dried and evaporated. The residue was chromatographed on silica gel, using CH2Cl2:MeOH 95:5 as eluent, to give the title compound in 40% yield.

Analogously, the following compounds can be prepared:
2-[2-(acetylamino)-1,3-thiazol-4-yl]-N-{5-[(3-hydroxypropyl)amino]-1,3-thiazol-2-yl}acetamide;
2-[2-(acetylamino)-1,3-thiazol-4-yl]-N-{5-[(2-hydroxyethyl)(methyl)amino]-1,3-thiazol-2-yl}acetamide;
2-[2-(acetylamino)-1,3-thiazol-4-yl]-N-{5-[(2-hydroxyethyl)amino]-1,3-thiazol-2-yl}acetamide; and
2-[4-(dimethylamino)phenyl]-N-{5-[(2-hydroxyethyl)amino]-1,3-thiazol-2-yl}acetamide;
2-[4-(dimethylamino)phenyl]-N-{5-[(2-hydroxyethyl)(methyl)amino]-1,3-thiazol-2-yl}acetamide;
2-[4-(dimethylamino)phenyl]-N-{5-[(3-hydroxypropyl)(methyl)amino]-1,3-thiazol-2-yl}acetamide; and
2-[4-(dimethylamino)phenyl]-N-{5-[(3-hydroxypropyl)amino]-1,3-thiazol-2-yl}acetamide.

Obviously, numerous modifications and variations of the present invention are possible in light of the above teachings. It is therefore to be understood that within the scope of the appended claims, the invention may be practiced otherwise than as specifically described herein.

What is claimed is:

1. A method for the treatment of cell proliferative disorders associated with an altered cell dependent kinase activity, comprising
administering to a mammal in need thereof a fixed dose combination product comprising
(A) an effective amount of a compound represented by formula (I) or (II):

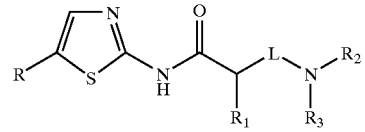

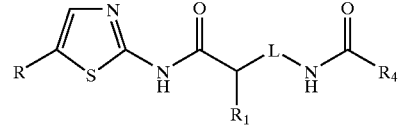

wherein L is a phenyl group or a 5 or 6 membered aromatic heterocycle with one or more heteroatoms selected from the group consisting of nitrogen, oxygen and sulfur;

R is (i) a halogen atom, a nitro group, or a group selected from the group consisting of pyrrolidino, morpholino, piperazino, N-alkyl piperazino, N-aryl-piperazino, N-arylalkyl-piperazino, piperidino and azabicyclo [3.2.2]nonane; or (ii) an amino group optionally further substituted with one or more groups, which may be the same or different, selected from the group consisting of alkyl, aryl, arylalkyl, alkylsulphonyl, arylsulphonyl, arylalkylsulphonyl, alkylcarbonyl, arylcarbonyl, and arylalkylcarbonyl, wherein the alkyl moieties therein are optionally further substituted with one or more hydroxy or amino groups; or (iii) a $C_3$–$C_6$ cycloalkyl optionally substituted with a straight or branched $C_1$–$C_6$ alkyl group; or (iv) a straight or branched $C_3$–$C_6$ alkyl group or an arylalkyl group which is optionally substituted with one or more substituents selected from the group consisting of halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl arylalkylcarbonyl, alkylsulphonyl, arylsulphonyl, arylalkylsulphonyl, aminosulphonyl, alkylaminosulphonyl, dialkylaminosulphonyl, alkylcarbonylamino, arylalkylcarbonylamino, arylaminosulphonyl, arylalkylaminosulphonyl, arylcarbonylamino, alkylsulphonylamino, arylsulphonylamino, arylalkylsulphonylamino, alkoxycarbonyl, aryloxycarbonyl, aminocarbonyl, alkylaminocarbonyl, arylaminocarbonyl, dialkylaminocarbonyl, arylalkylaminocarbonyl, pyrrolidino, morpholino, piperazino, N-alkylpiperazino, N-aryl-piperazino, N-arylalkylpiperazino, piperidino, and azabicyclo [3.2.2]nonane; or (v) an aryl group which is optionally substituted with one or more substituents selected from the group consisting of halogen, cyano, carboxy, hydroxy, nitro, alkylthio, alkoxy, straight or branched $C_1-C_6$ alkyl, arylthio, aryloxy, amino, alkylamino, dialkylamino, arylamino, arylalkylamino, hydroxyaminocarbonyl, alkoxyaminocarbonyl, $C_2-C_4$ alkenyl, $C_2-C_4$ alkynyl, $C_3-C_6$ cycloalkyl, alkyl-$C_3-C_6$ cycloalkyl, alkylcarbonyl, arylcarbonyl, arylalkylcarbonyl, alkylsulphonyl, arylsulphonyl, arylalkylsulphonyl, aminosulphonyl, alkylaminosulphonyl, dialkylaminosulphonyl, alkylcarbonylamino, arylalkylcarbonylamino, arylaminosulphonyl, arylalkylaminosulphonyl, arylcarbonylamino, alkylsulphonylamino, arylsulphonylamino, arylalkylsulphonylamino, alkoxycarbonyl, aryloxycarbonyl, aminocarbonyl, alkylaminocarbonyl, arylaminocarbonyl, dialkylaminocarbonyl, arylalkylaminocarbonyl, pyrrolidino, morpholino, piperazino, N-alkylpiperazino, N-arylpiperazino, N-arylalkyl-piperazino, piperidino, and azabicyclo[3.2.2]nonane;

$R_1$ is a hydrogen atom or a straight or branched $C_1-C_4$ alkyl group optionally substituted with one or more hydroxy, alkoxy, amino, alkylamino, or dialkylamino groups;

$R_2$ and $R_3$, which may be the same or different, are a hydrogen atom, a cycloalkyl group, a straight or branched $C_1-C_6$ alkyl group or an aryl group, which are each optionally substituted as described above for R; or $R_2$ and $R_3$, together with the nitrogen atom to which they are bonded, form a 4-morpholinyl, 1-piperazinyl, N-alkyl-piperazinyl, N-aryl-piperazinyl, N-arylalkyl-piperazinyl, piperidinyl, pyrrolidinyl, 2-oxo-1-pyrrolidinyl, imidazolyl or 3-azabicyclo[3.2.2]nonyl ring;

$R_4$ is carboxy, a perfluorinated alkyl group, a $C_2-C_4$ alkynyl group, 2-oxo-pyrrolidinyl, piperidinyl or a straight or branched $C_1-C_6$ alkyl group or an aryl group, which is optionally substituted as described above for R;

or a pharmaceutically acceptable salt thereof, and (B) an effective amount of one or more pharmaceutically active agents selected from the group consisting of antibiotic-type agents, alkylating agents, antimetabolite agents, hormonal agents, immunological agents, interferon-type agents, cyclooxygenase inhibitors, metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, ras-raf signal transduction pathway inhibitors, cell cycle inhibitors, cdks inhibitors, tubulin binding agents, topoisomerase I inhibitors, topoisomerase II inhibitors, and chemotherapeutic agents.

2. The method of claim 1, wherein the cell proliferative disorder is selected from the group consisting of cancer, Alzheimer's disease, viral infections, auto-immune diseases, and neurodegenerative disorders.

3. The method of claim 2, wherein the cancer is selected from the group consisting of carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xenoderoma pigmentosum, keratoctanthoma, thyroid follicular cancer, and Kaposi's sarcoma.

4. The method of claim 1, wherein the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis, and post-surgical stenosis and restenosis.

5. The method of claim 1, which provides tumor angiogenesis and metastasis inhibition.

6. The method of claim 1, which provides cell cycle inhibition or cdk/cyclin dependent inhibition.

7. The method of claim 1, further comprising subjecting the mammal in need thereof to a radiation therapy or chemotherapy regimen in combination with at least one cytostatic or cytotoxic agent.

8. The method of claim 1, wherein the (A) compound is represented by formula (I).

9. The method of claim 1, wherein the (A) compound is represented by formula (II).

10. The method of claim 1, wherein for the (A) compound

L is selected from the group consisting of phenyl, thiazole, imidazole, oxazole, pyrazole, isoxazole, thiophene, pyridine and pyrimidine;

R is (i) a halogen atom, (ii) a group selected from the group consisting of arylamino, alkylamino or dialkylamino, wherein the alkyl moiety is optionally further substituted with one or more hydroxy or amino groups, (iii) a $C_3-C_6$ cycloalkyl group optionally substituted with an alkyl group, (iv) a straight or branched $C_1-C_4$ alkyl or arylalkyl group, which is optionally substituted as described above, or (v) an optionally substituted aryl group;

$R_1$ is hydrogen or a $C_1-C_4$ alkyl group optionally substituted with a hydroxy or amino group; or a pharmaceutically acceptable salt thereof.

11. The method of claim 1, the (A) compound is selected from the group consisting of N-(4-{2-[(5-isopropyl-1,3-thiazol-2-yl)amino]-2-oxoethyl}-1,3-thiazol-2-yl) acrylamide;

N-(4-{2-[(5-isopropyl-1,3-thiazol-2-yl)amino]-2-oxoethyl}-1,3-thiazol-2-yl)-2-methylpropanamide;

N-(4-{2-[(5-isopropyl-1,3-thiazol-2-yl)amino]-2-oxoethyl}-1,3-thiazol-2-yl) -2-naphthamide;

N-(4-{2-[(5-isopropyl-1,3-thiazol-2-yl)amino]-2-oxoethyl}-1,3-thiazol-2-yl) benzamide;

N-(4-{2-[(5-isopropyl-1,3-thiazol-2-yl)amino]-2-oxoethyl}-1,3-thiazol-2-yl)-2-phenylacetamide;

N-(4-{2-[(5-isopropyl-1,3-thiazol-2-yl)amino]-2-oxoethyl}-1,3-thiazol-2-yl)-2-(3-pyridinyl)acetamide;

2,2,3,3,3-pentafluoro-N-(4-{2-[(5-isopropyl-1,3-thiazol-2-yl)amino]-2-oxoethyl}-1,3-thiazol-2-yl) propanamide;

2-[(4-{2-[(5-isopropyl-1,3-thiazol-2-yl)amino]-2-oxoethyl}-1,3-thiazol-2-yl)-amino]-2-oxoacetic acid;

2-fluoro-N-(4-{2-[(5-isopropyl-1,3-thiazol-2-yl)amino]-2-oxoethyl}-1,3-thiazol-2-yl)acetamide;

2-chloro-N-(4-{2-[(5-isopropyl-1,3-thiazol-2-yl)amino]-2-oxoethyl}-1,3-thiazol-2-yl)acetamide;

2-cyano-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl-3-oxo-beta-alanine;

N'1'-(4-{2-[(5-isopropyl-1,3-thiazol-2-yl)amino]-2-oxoethyl}-1,3-thiazol-2-yl) malonamide;

4-[(4-{2-[(5-isopropyl-1,3-thiazol-2-yl)amino]-2-oxoethyl}-1,3-thiazol-2-yl)-4-oxo-butanoic acid;

2-[2-(glycoloylamino)-1,3-thiazol-4-yl]-N-(5-isopropyl-1,3-thiazol-2-yl)acetamide;

3-hydroxy-N-(4-{2-[(5-isopropyl-1,3-thiazol-2-yl)amino]-2-oxoethyl}-1,3-thiazol-2-yl)propanamide;

3-amino-N-(4-{2-[(5-isopropyl-1,3-thiazol-2-yl)amino]-2-oxoethyl}1,3-thiazol-2-yl)propanamide;

2-amino-N-(4-{2-[(5-isopropyl-1,3-thiazol-2-yl)amino]-2-oxoethyl}-1,3-thiazol-2-yl)acetamide;

4-hydroxy-N-(4-{2-[(5-isopropyl-1,3-thiazol-2-yl)amino]-2-oxoethyl}-1,3-thiazol-2-yl)butanamide;

4-amino-N-(4-{2-[(5-isopropyl-1,3-thiazol-2-yl)amino]-2-oxoethyl}-1,3-thiazol-2-yl)butanamide;

N-(4-{2-[(5-isopropyl-1,3-thiazol-2-yl)amino]-2-oxoethyl}-1,3-thiazol-2-yl)-2-(4-methyl-1-piperazinyl)acetamide;

2-(4-benzyl-1-piperazinyl)-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-2-(1-piperidinyl)acetamide;

N-(5-isopropyl-1,3-thiazol-2-yl)-2-[2-(2-oxo-1-pyrrolidinyl)-1,3-thiazol-4-yl]acetamide;

2-[4-(dimethylamino)phenyl]-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-2-(1H-1,2,3,4-tetraazol-1-yl)acetamide;

N-(4-{2-[(5-isopropyl-1,3-thiazol-2-yl)amino]-2-oxoethyl}-1,3-thiazol-2-yl)-5-oxo-2-pyrrolidinecarboxamide;

N'1'-(4-{2-[(5-isopropyl-1,3-thiazol-2-yl)amino]-2-oxoethyl}-1,3-thiazol-2-yl)succinamide;

3-(1H-benzimidazol-2-yl)-N-(4-{2-[(5-isopropyl-1,3-thiazol-2-yl)amino]-2-oxoethyl}-1,3-thiazol-2-yl)propanamide;

1-acetyl-N-(4-{2-[(5-isopropyl-1,3-thiazol-2-yl)amino]-2-oxoethyl}-1,3-thiazol-2-yl)-4-piperidinecarboxamide;

2-[2-(acetylamino)-1,3-thiazol-4-yl]-N-(5-isopropyl-1,3-thiazol-2-yl)acetamide;

4-chloro-N-(4-{2-[(5-isopropyl-1,3-thiazol-2-yl)amino]-2-oxoethyl}-1,3-thiazol-2-yl)butanamide;

N-(4-{2-[(5-isopropyl-1,3-thiazol-2-yl)amino]-2-oxoethyl}-1,3-thiazol-2-yl)-2-methoxyacetamide;

3,3,3-trifluoro-N-(4-{2-[(5-isopropyl-1,3-thiazol-2-yl)amino]-2-oxoethyl)}-1,3-thiazol-2-yl)propanamide;

2-(dimethylamino)-N-(4-{2-[(5-isopropyl-1,3-thiazol-2-yl)amino]-2-oxoethyl}-1,3-thiazol-2-yl)acetamide;

N-(5-isopropyl-1,3-thiazol-2-yl)-2-(2-{[2-(4-methyl-1-piperazinyl)ethyl]amino}-1,3-thiazol-4-yl)acetamide R, R₁, L and R₄;

N-(5-isopropyl-1,3-thiazol-2-yl)-2-(2-{methyl[2-(4-methyl-1-piperazinyl)ethyl]amino}-1,3-thiazol-4-yl)acetamide;

N-(5-isopropyl-1,3-thiazol-2-yl)-2-(2-{[2-(4-morpholinyl)ethyl]amino}-1,3-thiazol-4-yl)acetamide;

N-(5-isopropyl-1,3-thiazol-2-yl)-2-(2-{methyl[2-(4-morpholinyl)ethyl]amino}-1,3-thiazol-4-yl)acetamide;

2-{2-[(2,3-dihydroxypropyl)amino]-1,3-thiazol-4-yl}-N-(5-isopropyl-1,3-thiazol-2-yl)acetamide;

2-{2-[(2,3-dihydroxypropyl)(methyl)amino]-1,3-thiazol-4-yl}-N-(5-isopropyl-1,3-thiazol-2-yl)acetamide;

2-(2-{[3-(dimethylamino)-2-hydroxypropyl]amino}-1,3-thiazol-4-yl)-N-(5-isopropyl-1,3-thiazol-2-yl)acetamide;

2-{2-[(2-amino-2-oxoethyl)amino]-1,3-thiazol-4-yl}-N-(5-isopropyl-1,3-thiazol-2-yl)acetamide;

2-(2-{[2-(dimethylamino)-2-oxoethyl]amino}-1,3-thiazol-4-yl)-N-(5-isopropyl-1,3-thiazol-2-yl)acetamide;

2-[2-(adamantylamino)-1,3-thiazol-4-yl]-N-(5-isopropyl-1,3-thiazol-2-yl)acetamide;

2-[4-(dimethylamino)phenyl]-N-(5-isopropyl-1,3-thiazol-2-yl)acetamide;

N-(5-isopropyl-1,3-thiazol-2-yl)-2-[4-(4-methyl-1-piperazinyl)phenyl]acetamide;

N-(5-isopropyl-1,3-thiazol-2-yl)-2-[4-(4-morpholinyl)phenyl]acetamide;

N-(5-isopropyl-1,3-thiazol-2-yl)-2-[4-(1-pyrrolidinyl)phenyl]acetamide;

N-(5-isopropyl-1,3-thiazol-2-yl)-2-(4-{[2-(4-methyl-1-piperazinyl)ethyl]amino}phenyl)acetamide;

N-(5-isopropyl-1,3-thiazol-2-yl)-2-(4-{methyl[2-(4-methyl-1-piperazinyl)ethyl]amino}phenyl)acetamide;

N-(5-isopropyl-1,3-thiazol-2-yl)-2-(4-{[2-(4-morpholinyl)ethyl]amino}phenyl)acetamide;

N-(5-isopropyl-1,3-thiazol-2-yl)-2-(4-{methyl[2-(4-morpholinyl)ethyl]amino}phenyl)acetamide;

2-{4-[(2,3-dihydroxypropyl)amino]phenyl}-N-(5-isopropyl-1,3-thiazol-2-yl)acetamide;

2-{4-[(2,3-dihydroxypropyl)(methyl)amino]phenyl}-N-(5-isopropyl-1,3-thiazol-2-yl)acetamide;

2-(4-{[3-(dimethylamino)-2-hydroxypropyl]amino}phenyl)-N-(5-isopropyl-1,3-thiazol-2-yl)acetamide;

2-[4-(1-adamantylamino)phenyl]-N-(5-isopropyl-1,3-thiazol-2-yl)acetamide;

2-{4-[(2-amino-2-oxoethyl)amino]phenyl}-N-(5-isopropyl-1,3-thiazol-2-yl)acetamide;

2-(4-{[2-(dimethylamino)-2-oxoethyl]amino}phenyl)-N-(5-isopropyl-1,3-thiazol-2-yl)acetamide;

2-[4-(acetylamino)phenyl]-N-(5-isopropyl-1,3-thiazol-2-yl)acetamide;

N-(4-{2-[(5-isopropyl-1,3-thiazol-2-yl)amino]-2-oxoethyl}phenyl)nicotinamide;

N-(4-{2-[(5-isopropyl-1,3-thiazol-2-yl)amino]-2-oxoethyl}phenyl)-5-methyl-2-thiophenecarboxamide;

N-(4-{2-[(5-isopropyl-1,3-thiazol-2-yl)amino]-2-oxoethyl}phenyl)-5-methyl-2-pyrazinecarboxamide;

N-(4-{2-[(5-isopropyl-1,3-thiazol-2-yl)amino]-2-oxoethyl}phenyl)-5-methyl-4-isoxazolecarboxamide;

N-(4-{2-[(5-isopropyl-1,3-thiazol-2-yl)amino]-2-oxoethyl}phenyl)-3,5-dimethyl-4-isoxazolecarboxamide;

(dimethylamino)-N-(4-{2-[(5-isopropyl-1,3-thiazol-2-yl)amino]-2-oxoethyl}phenyl)benzamide;

4-(acetylamino)-N-(4-{2-[(5-isopropyl-1,3-thiazol-2-yl)amino]-2-oxoethyl}phenyl)benzamide;

4-(dimethylamino)-N-(4-{2-[(5-isopropyl-1,3-thiazol-2-yl)amino]-2-oxoethyl}phenyl)benzamide;

N-(4-{2-[(5-isopropyl-1,3-thiazol-2-yl)amino]-2-oxoethyl}phenyl)-1,3-benzodoxole-5-carboxamide;

4-(aminosulfonyl)-N-(4-2-[(5-isopropyl-1,3-thiazol-2-yl)amino]-2-oxoethyl}phenyl)benzamide;

2-chloro-2,2-difluoro-N-(4-{2-[(5-isopropyl-1,3-thiazol-2-yl)amino]-2-oxoethyl}phenyl)acetamide;

2-cyano-N-(4-{2-[(5-isopropyl-1,3-thiazol-2-yl)amino]-2-oxoethyl}phenyl)acetamide;

1-acetyl-N-(4-{2-[(5-isopropyl-1,3-thiazol-2-yl)amino]-2-oxoethyl}phenyl)-4-piperidinecarboxamide;

N'1'-(4-{2-[(5-isopropyl-1,3-thiazol-2-yl)amino]-2-oxoethyl}phenyl)succinamide;

N-(4-{2-[(5-isopropyl-1,3-thiazol-2-yl)amino]-2-oxoethyl}phenyl)-2-methoxyacetamide;

3,3,3-trifluoro-N-(4-{2-[(5-isopropyl-1,3-thiazol-2-yl)amino]-2-oxoethyl}phenyl)propanamide;

N-(4-{2-[(5-isopropyl-1,3-thiazol-2-yl)amino]-2-oxoethyl}phenyl)-2-phenylacetamide;

N-(4-{2-[(5-isopropyl-1,3-thiazol-2-yl)amino]-2-oxoethyl}phenyl)-2-methoxy-2-phenylacetamide;

2-[4-(dimethylamino)phenyl]-N-(4-{2-[(5-isopropyl-1,3-thiazol-2-yl)amino]-2-oxoethyl}phenyl)acetamide;

N-(4-{2-[(5-isopropyl-1,3-thiazol-2-yl)amino]-2-oxoethyl}phenyl)-2-(3-pyridinyl)acetamide;

N-(4-{2-[(5-isopropyl-1,3-thiazol-2-yl)amino]-2-oxoethyl}phenyl)-2-(3-thienyl)acetamide;

N-(4-{2-[(5-isopropyl-1,3-thiazol-2-yl)amino]-2-oxoethyl}phenyl)-2-[5-(1-pyrrolidinyl)-2H-1,2,3,4-tetraazol-2-yl]acetamide;

2-cyclopropyl-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-5-methyl-2-pyrazinecarboxamide;

N-(4-{2-[(5-isopropyl-1,3-thiazol-2-yl)amino]-2-oxoethyl}-1,3-thiazol-2-yl)-2-propynamide;

N-(4-{2-[(5-isopropyl-1,3-thiazol-2-yl)amino]-2-oxoethyl}-1,3-thiazol-2-yl)-5-methyl-1,3-oxazole-4-carboxamide;

N-4-{2-[(5-isopropyl-1,3-thiazol-2-yl)amino]-2-oxoethyl}-1,3-thiazol-2-yl)-3,3-dimethylbutanamide;

N-(4-{2-[(5-isopropyl-1,3-thiazol-2-yl)amino]-2-oxoethyl}-1,3-thiazol-2-yl)-3-methyl-2-butenamide;

3-cyclopentyl-N-(4-{2-[(5-isopropyl-1,3-thiazol-2-yl)amino]-2-oxoethyl}-1,3-thiazol-2-yl)propanamide;

N-(4-{2-[(5-isopropyl-1,3-thiazol-2-yl)amino]-2-oxoethyl}-1,3-thiazol-2-yl)-2-(3-thienyl)acetamide;

N-(4-{2-[(5-isopropyl-1,3-thiazol-2-yl)amino]-2-oxoethyl}-1,3-thiazol-2-yl)-2-(3-pyridinyl)acetamide;

2,2,2-trifluoro-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-3-(2-thienyl)propanamide;

N-(4-{2-[(5-isopropyl-1,3-thiazol-2-yl)amino]-2-oxoethyl}-1,3-thiazol-2-yl)-2-(4-pyridinylsulfanyl)acetamide;

N-(4-{2-[(5-isopropyl-1,3-thiazol-2-yl)amino]-2-oxoethyl}-1,3-thiazol-2-yl)-2-(3-pyridinyl)-1,3-thiazole-4-carboxamide;

2-[2-(acetylamino)-1,3-thiazol-4-yl]-N-(5-cyclopropyl-1,3-thiazol-2-yl)acetamide;

2-[2-(acetylamino)-1,3-thiazol-4-yl]-N-{5-[(3-hydroxypropyl)(methyl)amino]-1,3-thiazol-2-yl}acetamide;

2-[2-(acetylamino)-1,3-thiazol-4-yl]-N-{5-[(2-hydroxyethyl)(methyl)amino]-1,3-thiazol-2yl}acetamide;

2-[4-(dimethylamino)phenyl]-N-{5-[(2-hydroxyethyl)(methyl)amino]-1,3-thiazol-2-yl}acetamide;

2-[4-(dimethylamino)phenyl]-N-{5-[(3-hydroxypropyl)(methyl)amino]-1,3-thiazol-2-yl)acetamide;

N-(5-cyclopropyl-1,3-thiazol-2-yl)-2-[4-(dimethylamino)phenyl]acetamide; and pharmaceutically acceptable salts thereof.

12. The method of claim 1, wherein the mammal is a human.

13. A fixed dose combination product for the treatment of cell proliferative disorders associated with an altered cell dependent kinase activity comprising (A) an effective amount of a 2-amino-1,3-thiazole derivative represented by formula (I) or (II):

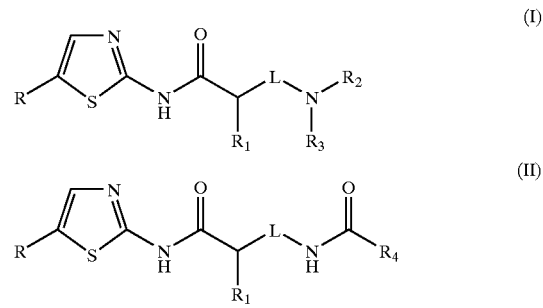

wherein L is a phenyl group or a 5 or 6 membered aromatic heterocycle with one or more heteroatoms selected from the group consisting of nitrogen, oxygen and sulfur;

R is (i) a halogen atom, a nitro group, or a group selected from the group consisting of pyrrolidino, morpholino, piperazino, N-alkyl piperazino, N-aryl-piperazino, N-arylalkyl-piperazino, piperidino and azabicyclo [3.2.2]nonane; or (ii) an amino group optionally further substituted with one or more groups, which may be the same or different, selected from the group consisting of alkyl, aryl, arylalkyl, alkylsulphonyl, arylsulphonyl, arylalkylsulphonyl, alkylcarbonyl, arylcarbonyl, and arylalkylcarbonyl, wherein the alkyl moieties therein are optionally further substituted with one or more hydroxy or amino groups; or (iii) a $C_3$–$C_6$ cycloalkyl optionally substituted with a straight or branched $C_1$–$C_6$ alkyl group; or (iv) a straight or branched $C_1$–$C_6$ alkyl group or an arylalkyl group which is optionally substituted with one or more substituents selected from the group consisting of halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl, arylalkylcarbonyl, alkylsulphonyl, arylsulphonyl, arylalkylsulphonyl, aminosulphonyl, alkylaminosulphonyl, dialkylaminosulphonyl, alkylcarbonylamino, arylalkylcarbonylamino, arylaminosulphonyl, arylalkylaminosulphonyl, arylcarbonylamino, alkylsulphonylamino, arylsulphonylamino, arylalkylsulphonylamino, alkoxycarbonyl, aryloxycarbonyl, aminocarbonyl, alkylaminocarbonyl, arylaminocarbonyl, dialkylaminocarbonyl, arylalkylaminocarbonyl, pyrrolidino, morpholino, piperazino, N-alkylpiperazino, N-aryl-piperazino, N-arylalkylpiperazino, piperidino, and azabicyclo [3.2.2]nonane; or (v) an aryl group which is optionally substituted with one or more substituents selected from the group consisting of halogen, cyano, carboxy, hydroxy, nitro, alkylthio, alkoxy, straight or branched $C_1$–$C_6$ alkyl, arylthio, aryloxy, amino, alkylamino, dialkylamino, arylamino, arylalkylamino, hydroxyaminocarbonyl, alkoxyaminocarbonyl, $C_2$–$C_4$ alkenyl, $C_2$–$C_4$ alkynyl, $C_3$–$C_6$ cycloalkyl, alkyl-$C_3$–$C_6$ cycloalkyl, alkylcarbonyl, arylcarbonyl, arylalkylcarbonyl, alkylsulphonyl, arylsulphonyl, arylalkylsulphonyl, aminosulphonyl, alkylaminosulphonyl, dialkylaminosulphonyl, alkylcarbonylamino, arylalkylcarbonylamino, arylaminosulphonyl, arylalkylaminosulphonyl, arylcarbonylamino, alkylsulphonylamino, arylsulphonylamino, arylalkylsulphonylamino, alkoxycarbonyl, aryloxycarbonyl, aminocarbonyl, alkylaminocarbonyl, arylaminocarbonyl, dialkylaminocarbonyl, arylalkylaminocarbonyl, pyrrolidino, morpholino, piperazino, N-alkylpiperazino, N-arylpiperazino, N-arylalkyl-piperazino, piperidino, and azabicyclo [3.2.2]nonane;

$R_1$ is a hydrogen atom or a straight or branched $C_1$–$C_4$ alkyl group optionally substituted with one or more hydroxy, alkoxy, amino, alkylamino, or dialkylamino groups;

$R_2$ and $R_3$, which may be the same or different, are a hydrogen atom, a cycloalkyl group, a straight or branched $C_1$–$C_6$ alkyl group or an aryl group, which are each optionally substituted as described above for R; or $R_2$ and $R_3$, together with the nitrogen atom to which they are bonded, form a 4-morpholinyl, 1-piperazinyl, N-alkyl-piperazinyl, N-aryl-piperazinyl, N-arylalkyl-piperazinyl, piperidinyl, pyrrolidinyl, 2-oxo-1-pyrrolidinyl, imidazolyl or 3-azabicyclo[3.2.2]nonyl ring;

$R_4$ is carboxy, a perfluorinated alkyl group, a $C_2$–$C_4$ alkynyl group, 2-oxo-pyrrolidinyl, piperidinyl or a straight or branched $C_1$–$C_6$ alkyl group or an aryl group, which is optionally substituted as described above for R;

or a pharmaceutically acceptable salt thereof, and (B) an effective amount of one or more pharmaceutically active agents selected from the group consisting of antibiotic-type agents, alkylating agents, antimetabolite agents, hormonal agents, immunological agents, interferon-type agents, cyclooxygenase inhibitors, metallomatrixprotease inhibitors, telomerase inhibitors, tyrosine kinase inhibitors, anti-growth factor receptor agents, anti-HER agents, anti-EGFR agents, antiangiogenesis agents, farnesyl transferase inhibitors, ras-raf signal transduction pathway inhibitors, cell cycle inhibitors, cdks inhibitors, tubulin binding agents, topoisomerase I inhibitors, topoisomerase II inhibitors, and chemotherapeutic agents.

14. The fixed dose combination product of claim 13 in which the 2-amino-1,3-thiazole derivative is represented by formula (I).

15. The fixed dose combination product of claim 13 in which the 2-amino-1,3-thiazole derivative is represented by formula (II).

16. The fixed dose combination product of claim 13, wherein as to the 2-amino-1,3-thiazole derivative L is selected from the group consisting of phenyl, thiazole, imidazole, oxazole, pyrazole, isoxazole, thiophene, pyridine and pyrimidine;

R is (i) a halogen atom, (ii) a group selected from the group consisting of arylamino, alkylamino or dialkylamino, wherein the alkyl moiety is optionally further substituted with one or more hydroxy or amino groups, (iii) a $C_3$–$C_6$ cycloalkyl group optionally substituted with an alkyl group, (iv) a straight or branched $C_1$–$C_4$ alkyl or arylalkyl group, which is optionally substituted as described above, or (v) an optionally substituted aryl group;

$R_1$ is hydrogen or a $C_1$–$C_4$ alkyl group optionally substituted with a hydroxy or amino group;

or a pharmaceutically acceptable salt thereof.

17. The fixed dose combination product of claim 13 in which the 2-amino-1,3-thiazole derivative is selected from the group consisting of N-(4-{2-[(5-isopropyl-1,3-thiazol-2-yl)amino]-2-oxoethyl}-1,3-thiazol-2-yl) acrylamide;

N-(4-{2-[(5-isopropyl-1,3-thiazol-2-yl)amino]-2-oxoethyl}-1,3-thiazol-2-yl)-2-methylpropanamide;

N-(4-{2-[(5-isopropyl-1,3-thiazol-2-yl)amino]-2-oxoethyl}-1,3-thiazol-2-yl)-2-naphthamide;

N-(4-{2-[(5-isopropyl-1,3-thiazol-2-yl)amino]-2-oxoethyl}-1,3-thiazol-2-yl) benzamide;

N-(4-{2-[(5-isopropyl-1,3-thiazol-2-yl)amino]-2-oxoethyl}-1,3-thiazol-2-yl)-2-phenylacetamide;

N-(4-{2-[(5-isopropyl-1,3-thiazol-2-yl)amino]-2-oxoethyl}-1,3-thiazol-2-(3-pyridinyl)acetamide;

2,2,3,3,3-pentafluoro-N-(4-{2-[(5-isopropyl-1,3-thiazol-2-yl)amino]-2-oxoethyl}-1,3-thiazol-2-yl) propanamide;

2-[(4-{2-[(5-isopropyl-1,3-thiazol-2-yl)amino]-2-oxoethyl}-1,3-thiazol-2-yl)amino]-2-oxoacetic acid;

2-fluoro-N-(4-{2-[(5-isopropyl-1,3-thiazol-2-yl)amino]-2-oxoethyl}-1,3-thiazol-2-yl)acetamide;

2-chloro-N-(4-{2-[(5-isopropyl-1,3-thiazol-2-yl)amino]-2-oxoethyl}-1,3-thiazol-2-yl)acetamide;

2-cyano-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl-3-oxo-beta-alanine;

N'1'-(4-{2-[(5-isopropyl-1,3-thiazol-2-yl)amino]-2-oxoethyl}-1,3-thiazol-2-yl)malonamide;

4-[(4-{2-[(5-isopropyl-1,3-thiazol-2-yl)amino]-2-oxoethyl}-1,3-thiazol-2-yl)-4-oxo-butanoic acid;

2-[2-(glycoloylamino)-1,3-thiazol-4-yl]-N-(5-isopropyl-1,3-thiazol-2-yl)acetamide;

3-hydroxy-N-(4-{2-[(5-isopropyl-1,3-thiazol-2-yl)amino]-2-oxoethyl}-1,3-thiazol-2-yl)propanamide;

3-amino-N-(4-{2-[(5-isopropyl-1,3-thiazol-2-yl)amino]-2-oxoethyl}-1,3-thiazol-2-yl)propanamide;

2-amino-N-(4-{2-[(5-isopropyl-1,3-thiazol-2-yl)amino]-2-oxoethyl}-1,3-thiazol-2-yl)acetamide;

4-hydroxy-N-(4-{2-[(5-isopropyl-1,3-thiazol-2-yl)amino]-2-oxoethyl}-1,3-thiazol-2-yl)butanamide;

4-amino-N-(4-{2-[(5-isopropyl-1,3-thiazol-2-yl)amino]-2-oxoethyl}-1,3-thiazol-2-yl)butanamide;

N-(4-{2-[(5-isopropyl-1,3-thiazol-2-yl)amino]-2-oxoethyl}-1,3-thiazol-2-yl)-2-(4-methyl-1-piperazinyl)acetamide;

2-(4-benzyl-1-piperazinyl)-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-2-(1-piperidinyl)acetamide;

N-(5-isopropyl-1,3-thiazol-2-yl)-2-[2-(2-oxo-1-pyrrolidinyl)-1,3-thiazol-4-yl]acetamide;

2-[4-(dimethylamino)phenyl]-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-2-(1H-1,2,3,4-tetraazol-1-yl)acetamide;

N-(4-{2-[(5-isopropyl-1,3-thiazol-2-yl)amino]-2-oxoethyl}-1,3-thiazol-2-yl)-5-oxo-2-pyrrolidinecarboxamide;

N'1'-(4-{2-[(5-isopropyl-1,3-thiazol-2-yl)amino]-2-oxoethyl}-1,3-thiazol-2-yl)succinamide;

3-(1H-benzimidazol-2-yl)-N-(4-{2-[(5-isopropyl-1,3-thiazol-2-yl)amino]-2-oxoethyl}-1,3-thiazol-2-yl)propanamide;

1-acetyl-N-(4-{2-[(5-isopropyl-1,3-thiazol-2-yl)amino]-2-oxoethyl}-1,3-thiazol-2-yl)-4-piperidinecarboxamide;

2-[2-(acetylamino)-1,3-thiazol-4-yl]-N-(5-isopropyl-1,3-thiazol-2-yl)acetamide;

4-chloro-N-(4-{2-[(5-isopropyl-1,3-thiazol-2-yl)amino]-2-oxoethyl}-1,3-thiazol-2-yl)butanamide;

N-(4-{2-[(5-isopropyl-1,3-thiazol-2-yl)amino]-2-oxoethyl}-1,3-thiazol-2-yl)-2-methoxyacetamide;

3,3,3-trifluoro-N-(4-{2-[(5-isopropyl-1,3-thiazol-2-yl)amino]-2-oxoethyl}-1,3-thiazol-2-yl)propanamide;

2-(dimethylamino)-N-(4-{2-[(5-isopropyl-1,3-thiazol-2-yl)amino]-2-oxoethyl}-1,3-thiazol-2-yl)acetamide;

N-(5-isopropyl-1,3-thiazol-2-yl)-2-(2-{[2-(4-methyl-1-piperazinyl)ethyl]amino}-1,3-thiazol-4-yl)acetamide;

N-(5-isopropyl-1,3-thiazol-2-yl)-2-(2-{methyl[2-(4-methyl-1-piperazinyl)ethyl]amino}-1,3-thiazol-4-yl)acetamide, N-(5-isopropyl-1,3-thiazol-2-yl)-2-(2-{[2-(4-morpholinyl)ethyl]amino}-1,3-thiazol-4-yl)acetamide;

N-(5-isopropyl-1,3-thiazol-2-yl)-2-(2-{methyl[2-(4-morpholinyl)ethyl]amino}1,3-thiazol-4-yl)acetamide;

2-{2-[(2,3-dihydroxypropyl)amino]-1,3-thiazol-4-yl}-N-(5-isopropyl-1,3-thiazol-2-yl)acetamide;

2-{2-[(2,3-dihydroxypropyl)(methyl)amino]-1,3-thiazol-4-yl}-N-(5-isopropyl-1,3-thiazol-2-yl)acetamide;

2-(2-{[3-(dimethylamino)-2-hydroxypropyl]amino}-1,3-thiazol-4-yl)-N-(5-isopropyl-1,3-thiazol-2-yl)acetamide;

2-{2-[(2-amino-2-oxoethyl)amino]-1,3-thiazol-4-yl}-N-(5-isopropyl-1,3-thiazol-2-yl)acetamide;

2-(2-{[2-(dimethylamino)-2-oxoethyl]amino}-1,3-thiazol-4-yl)-N-(5-isopropyl-1,3-thiazol-2-yl)acetamide;

2-[2-(adamantylamino)-1,3-thiazol-4-yl]-N-(5-isopropyl-1,3-thiazol-2-yl)acetamide;

2-[4-(dimethylamino)phenyl]-N-(5-isopropyl-1,3-thiazol-2-yl)acetamide;

N-(5-isopropyl-1,3-thiazol-2-yl)-2-[4-(4-methyl-1-piperazinyl)phenyl]acetamide;

N-(5-isopropyl-1,3-thiazol-2-yl)-2-[4-(4-morpholinyl)phenyl]acetamide;

N-(5-isopropyl-1,3-thiazol-2-yl)-2-[4-(1-pyrrolidinyl)phenyl]acetamide;

N-(5-isopropyl-1,3-thiazol-2-yl)-2-(4-{[2-(4-methyl-1-piperazinyl)ethyl]amino}phenyl)acetamide;

N-(5-isopropyl-1,3-thiazol-2-yl)-2-(4-{methyl[2-(4-methyl-1-piperazinyl)ethyl]amino}phenyl)acetamide;

N-(5-isopropyl-1,3-thiazol-2-yl)-2-(4-{[2-(4-morpholinyl)ethyl]amino}phenyl)acetamide;

N-(5-isopropyl-1,3-thiazol-2-yl)-2-(4-{methyl[2-(4-morpholinyl)ethyl]amino}phenyl)acetamide;

2-{4-[(2,3-dihydroxypropyl)amino]phenyl}-N-(5-isopropyl-1,3-thiazol-2-yl)acetamide;

2-{4-[(2,3-dihydroxypropyl)(methyl)amino]phenyl}-N-(5-isopropyl-1,3-thiazol-2-yl)acetamide;

2-(4-{[3-(dimethylamino)-2-hydroxypropyl]amino}phenyl)-N-(5-isopropyl-1,3-thiazol-2-yl)acetamide, 2-[4-(1-adamantylamino)phenyl]-N-(5-isopropyl-1,3-thiazol-2-yl)acetamide, 2-{4-[(2-amino-2-oxoethyl)amino]phenyl}-N-(5-isopropyl-1,3-thiazol-2-yl)acetamide;

2-(4-{[2-(dimethylamino)-2-oxoethyl]amino}phenyl)-N-(5-isopropyl-1,3-thiazol-2-yl)acetamide;

2-[4-(acetylamino)phenyl]-N-(5-isopropyl-1,3-thiazol-2-yl)acetamide;

N-(4-{2-[(5-isopropyl-1,3-thiazol-2-yl)amino]-2-oxoethyl}phenyl)nicotinamide;

N-(4-{2-[(5-isopropyl-1,3-thiazol-2-yl)amino]-2-oxoethyl}phenyl)-5-methyl-2-thiophenecarboxamide, N-(4-{2-[(5-isopropyl-1,3-thiazol-2-yl)amino]-2-oxoethyl}phenyl)-5-methyl-2-pyrazinecarboxamide;

N-(4-{2-[(5-isopropyl-1,3-thiazol-2-yl)amino]-2-oxoethyl}phenyl)-5-methyl-4-isoxazolecarboxamide;

N-(4-{2-[(5-isopropyl-1,3-thiazol-2-yl)amino]-2-oxoethyl}phenyl)-3,5-dimethyl-4-isoxazolecarboxamide;

(dimethylamino)-N-(4-{2-[(5-isopropyl-1,3-thiazol-2-yl)amino]-2-oxoethyl}phenyl)benzamide;

4-(acetylamino)-N-(4-{2-[(5-isopropyl-1,3-thiazol-2-yl)amino]-2-oxoethyl}phenyl)benzamide, 4-(dimethylamino)-N-(4-{2-[(5-isopropyl-1,3-thiazol-2-yl)amino]-2-oxoethyl}phenyl)benzamide;

N-(4-{2-[(5-isopropyl-1,3-thiazol-2-yl)amino]-2-oxoethyl}phenyl)-1,3-benzodoxole-5-carboxamide;

4-(aminosulfonyl)-N-(4-{2-[(5-isopropyl-1,3-thiazol-2-yl)amino]-2-oxoethyl}phenyl)benzamide;

2-chloro-2,2-difluoro-N-(4-{2-[(5-isopropyl-1,3-thiazol-2-yl)amino]-2-oxoethyl}phenyl)acetamide;

2-cyano-N-(4-{2-[(5-isopropyl-1,3-thiazol-2-yl)amino]-2-oxoethyl}phenyl)acetamide;

1-acetyl-N-(4-{2-[(5-isopropyl-1,3-thiazol-2-yl)amino]-2-oxoethyl}phenyl)-4-piperidinecarboxamide;

N'1'-(4-{2-[(5-isopropyl-1,3-thiazol-2-yl)amino]-2-oxoethyl}phenyl)succinamide;

N-(4-{2-[(5-isopropyl-1,3-thiazol-2-yl)amino]-2-oxoethyl}phenyl)-2-methoxyacetamide;

3,3,3-trifluoro-N-(4-{2-[(5-isopropyl-1,3-thiazol-2-yl)amino]-2-oxoethyl}phenyl)propanamide;

N-(4-{2-[(5-isopropyl-1,3-thiazol-2-yl)amino]-2-oxoethyl}phenyl)-2-phenylacetamide;

N-(4-{2-[(5-isopropyl-1,3-thiazol-2-yl)amino]-2-oxoethyl}phenyl)-2-methoxy-2-phenylacetamide;

2-[4-(dimethylamino)phenyl]-N-(4-{2-[(5-isopropyl-1,3-thiazol-2-yl) amino]-2-oxoethyl}phenyl)acetamide;

N-(4-{2-[(5-isopropyl-1,3-thiazol-2-yl)amino]-2-oxoethyl}phenyl)-2-(3-pyridinyl)acetamide;

N-(4-{2-[(5-isopropyl-1,3-thiazol-2-yl)amino]-2-oxoethyl}phenyl)-2-(3-thienyl)acetamide;

N-(4-{2-[(5-isopropyl-1,3-thiazol-2-yl)amino]-2-oxoethyl}phenyl)-2-[5-(1-pyrrolidinyl)-2H-1,2,3,4-tetraazol-2-yl]acetamide;

2-cyclopropyl-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-5-methyl-2-pyrazinecarboxamide;

N-(4-{2-[(5-isopropyl-1,3-thiazol-2-yl)amino]-2-oxoethyl}-1,3-thiazol-2-yl)-2-propynamide;

N-(4-{2-[(5-isopropyl-1,3-thiazol-2-yl)amino]-2-oxoethyl}-1,3-thiazol-2-yl)-5-methyl-1,3-oxazole4-carboxamide;

N-4-{2-[(5-isopropyl-1,3-thiazol-2-yl)amino]-2-oxoethyl}-1,3-thiazol-2-yl)-3,3-dimethylbutanamide;

N-(4-{2-[(5-isopropyl-1,3-thiazol-2-yl)amino]-2-oxoethyl}-1,3-thiazol-2-yl)-3methyl-2-butenamide;

3-cyclopentyl-N-(4-{2-[(5-isopropyl-1,3-thiazol-2-yl)amino]-2-oxoethyl}-1,3-thiazol-2-yl)propanamide;

N-(4-(2-[(5-isopropyl-1,3-thiazol-2-yl)amino]-2-oxoethyl}-1,3-thiazol-2-yl)-2-(3-thienyl)acetamide;

N-(4-{2-[(5-isopropyl-1,3-thiazol-2-yl)amino]-2-oxoethyl}-1,3-thiazol-2-yl)-2-(3-pyridinyl)acetamide;

2,2,2-trifluoro-N-(4-{2-[(5-isopropyl-1,3-thiazol-2-yl)amino]-2-oxoethyl}-1,3-thiazol-2-yl)acetamide;

N-(4-{2-[(5-isopropyl-1,3-thiazol-2-yl)amino]-2-oxoethyl}-1,3-thiazol-2-yl)-3-(2-thienyl)propanamide;

N-(4-{2-[(5-isopropyl-1,3-thiazol-2-yl)amino]-2-oxoethyl}-1,3-thiazol-2-yl)-2-(4-pyridinylsulfanyl)acetamide;

N-(4-{2-[(5-isopropyl-1,3-thiazol-2-yl)amino]-2-oxoethyl}-1,3-thiazol-2-yl)-2-(3-pyridinyl)-1,3-thiazole-4-carboxamide;

2-[2-(acetylamino)-1,3-thiazol-4-yl]-N-(5-cyclopropyl-1,3-thiazol-2-yl)acetamide;

2-[2-(acetylamino)-1,3-thiazol-4-yl]-N-{5-[(3-hydroxypropyl)(methyl)amino]-1,3-thiazol-2-yl}acetamide;

2-[2-(acetylamino)-1,3-thiazol-4-yl]-N-{5-[(2-hydroxyethyl)(methyl)amino]-1,3-thiazol-2yl}acetamide;

2-[4-(dimethylamino)phenyl]-N-{5-[(2-hydroxyethyl)(methyl)amino]-1,3-thiazol-2-yl}acetamide;

2-[4-(dimethylamino)phenyl]-N-{5-[(3-hydroxypropyl)(methyl)amino]-1,3-thiazol-2-yl}acetamide;

N-(5-cyclopropyl-1,3-thiazol-2-yl)-2-[4-(dimethylamino)phenyl]acetamide; and pharmaceutically acceptable salts thereof.

\* \* \* \* \*